(12) United States Patent
Toll et al.

(10) Patent No.: US 9,156,069 B2
(45) Date of Patent: Oct. 13, 2015

(54) APPARATUS AND PROCESS FOR TREATING WASTE

(75) Inventors: Ian Cecil Toll, Dorset (GB); Christian Andrew Ian Toll, Dorset (GB); Nigel Anthony Bailey, Dorset (GB); Zhengjian Wang, Dorset (GB)

(73) Assignee: Aerothermal Group Limited (GB)

( * ) Notice: Subject to any disclaimer, the term of this patent is extended or adjusted under 35 U.S.C. 154(b) by 519 days.

(21) Appl. No.: 13/575,268

(22) PCT Filed: Jan. 28, 2011

(86) PCT No.: PCT/GB2011/050145
§ 371 (c)(1),
(2), (4) Date: Oct. 5, 2012

(87) PCT Pub. No.: WO2011/092509
PCT Pub. Date: Aug. 4, 2011

(65) Prior Publication Data
US 2013/0029394 A1    Jan. 31, 2013

(30) Foreign Application Priority Data

Jan. 28, 2010  (GB) .................................. 1001375.3

(51) Int. Cl.
*B09B 3/00* (2006.01)
*A61L 11/00* (2006.01)
*B01J 19/28* (2006.01)

(52) U.S. Cl.
CPC . *B09B 3/00* (2013.01); *A61L 11/00* (2013.01); *B01J 19/28* (2013.01); *B09B 3/0091* (2013.01); *Y02E 50/343* (2013.01); *Y02W 30/20* (2013.01)

(58) Field of Classification Search
CPC ........ B09B 3/00; B09B 3/0091; A61L 11/00; B01J 19/28

USPC ............................................................ 422/26
See application file for complete search history.

(56) References Cited

U.S. PATENT DOCUMENTS 2,841,308 A   7/1958   Weicker
2,936,093 A   5/1960   Passalaqua
(Continued)

FOREIGN PATENT DOCUMENTS

FR   2927983 A   8/2009
GB    593205 A   10/1947
(Continued)

OTHER PUBLICATIONS

"International Application Serial No. PCT/GB2011/050145, International Preliminary Report on Patentability mailed Aug. 9, 2012", 14 pgs.
(Continued)

*Primary Examiner* — Regina M Yoo
(74) *Attorney, Agent, or Firm* — Schwegman Lundberg & Woessner, P.A.

(57) ABSTRACT

Solid waste to be treated is introduced into the interior of a rotary autoclave that is downwardly inclined towards its discharge end and has a door at the discharge end. Steam is injected through said door via a plenum chamber in the door so that water and steam pass through a one-way device and then directly into the interior of the autoclave. The one-way device prevents the solid waste from entering the plenum chamber from the interior of the autoclave. The plenum chamber is defined between a region of the door and a plate secured to the door at a small spacing inwardly of the door. The outlet is defined in the plate and the one one-way device is fitted to the outlet.

15 Claims, 22 Drawing Sheets

(56) References Cited

U.S. PATENT DOCUMENTS

| | | | |
|---|---|---|---|
| 3,804,288 A | | 4/1974 | Piegza |
| 3,811,148 A | | 5/1974 | Martin |
| 4,254,152 A | * | 3/1981 | Janovtchik ............... 426/399 |
| 4,540,495 A | | 9/1985 | Holloway |
| 4,571,270 A | * | 2/1986 | Sasaki ......................... 134/5 |
| 4,710,350 A | * | 12/1987 | Petersen ...................... 422/37 |
| 4,822,397 A | * | 4/1989 | Crossley ..................... 65/107 |
| 4,844,351 A | | 7/1989 | Holloway |
| 4,974,781 A | | 12/1990 | Placzek |
| 5,119,994 A | | 6/1992 | Placzek |
| 5,427,650 A | | 6/1995 | Holloway |
| 5,439,655 A | * | 8/1995 | Fedegari ................... 422/297 |
| 5,445,329 A | | 8/1995 | Anderson |
| 5,478,985 A | * | 12/1995 | Hoetzl et al. ............... 219/400 |
| 5,655,718 A | | 8/1997 | Anderson |
| 5,666,878 A | * | 9/1997 | Taricco ....................... 100/73 |
| 7,347,391 B2 | | 3/2008 | Michalek et al. |
| 7,968,057 B2 | * | 6/2011 | Burrows .................... 422/297 |
| 8,431,085 B2 | * | 4/2013 | Froderberg et al. ......... 422/295 |
| 2002/0085945 A1 | * | 7/2002 | Florkey et al. ............... 422/3 |
| 2007/0190643 A1 | | 8/2007 | Noll |
| 2007/0231885 A1 | | 10/2007 | Choate et al. |
| 2008/0202993 A1 | * | 8/2008 | Eley et al. .................. 210/130 |
| 2008/0217444 A1 | | 9/2008 | Michalek et al. |
| 2010/0129257 A1 | | 5/2010 | Michalek et al. |
| 2013/0243662 A1 | * | 9/2013 | Froderberg et al. .......... 422/295 |

FOREIGN PATENT DOCUMENTS

| | | |
|---|---|---|
| GB | 2233340 A | 1/1991 |
| JP | 09-271744 A | 10/1997 |
| WO | WO-82/01483 A1 | 5/1982 |
| WO | WO-00/72987 A1 | 12/2000 |
| WO | WO-02/070101 A2 | 9/2002 |
| WO | WO-03/024633 A1 | 3/2003 |
| WO | WO-2004/041733 A1 | 5/2004 |
| WO | WO-2006/015423 A1 | 2/2006 |
| WO | WO-2006/056768 A2 | 6/2006 |
| WO | WO-2008/081028 A2 | 7/2008 |
| WO | WO-2009/095693 A2 | 8/2009 |
| WO | WO-2009/101393 A2 | 8/2009 |
| WO | WO-2010/010071 A2 | 1/2010 |

OTHER PUBLICATIONS

"Great Britain Application Serial No. GB1001375.3, Search Report mailed Mar. 25, 2010", 5 pgs.

"Great Britain Application Serial No. GB1001375.3, Search Report mailed Jun. 21, 2010", 3 pgs.

"Great Britain Application Serial No. GB1001493.2, Combined Search and Examination Report mailed Feb. 8, 2011", 7 pgs.

"Great Britian Application Serial No. GB110500.5, Combined Search and Examination Report mailed Feb. 7, 2011", 9 pgs.

"International Application Serial No. PCT/GB2011/050145, International Search Report mailed Aug. 26, 2011", 6 pgs.

"International Application Serial No. PCT/GB2011/050145, Written Opinion mailed Aug. 26, 2011", 14 pgs.

\* cited by examiner

SECTION A-A

APPARATUS AND PROCESS FOR TREATING WASTE

RELATED APPLICATIONS

This application is a nationalization under 35 U.S.C. 371 of PCT/GB2011/050145, filed Jan. 28, 2011 and published as WO 2011/092509 on Aug. 4, 2011, which claims priority to United Kingdom Patent Application Serial No. 1001375.3, filed Jan. 28, 2010; which applications and publication are incorporated herein by reference in their entirety.

FIELD OF THE INVENTION

This invention relates to apparatus and to a process for the treatment of waste including but not limited to municipal solid waste (MSW). Suitable waste will be normally classified as non-hazardous and non-toxic and may be at least in part biodegradable or may be wholly biodegradable. Its composition may depend on the extent of pre-sorting demanded by a municipality. It may include household waste or sorted fractions of household waste, catering waste (including waste from restaurants or other catering facilities), biodegradable supermarket waste, paper and biodegradable plastics waste, partly or wholly biodegradable commercial waste or mixtures thereof. It may include food and kitchen waste and paper or other organic materials waste and as a component non-biodegradable recyclable waste e.g. plastics, glass or a mixture thereof. It may also include specialised wastes such as animal and fish-based waste e.g. slaughterhouse waste, shellfish waste, poultry product waste and supermarket food waste.

BACKGROUND TO THE INVENTION

U.S. Pat. No. 4,540,495 (Holloway, 1985, the disclosure of which is incorporated herein by reference) is concerned with a process for the treatment of municipal solid waste (MSW). It discloses that the waste comprises inorganic, organic and synthetic fractions. The major portion of the inorganic fraction is said to be metal and glass containers, ceramics, masonry, building materials and the like. The organic fraction which is stated to comprise 80 wt % of MSW consists of lignocellulose e.g. paper products together with yard (garden) waste and food waste. The synthetic fraction comprises plastics containers, plastics film and other synthetic plastics products. The organic fraction is said to represent the industrial world's largest economically accessible source of lignocellulose feedstock for conversion into alcohol and other industrial chemicals. It is further explained that MSW is an environmental concern owing to the dwindling availability of landfill sites. A treatment process is disclosed in which MSW is fed into a pressure vessel, subjected to heat at 132-160° C. (270-320° F.) under a pressure of from 276-517 kPa (40 to 75 psi) for 30-90 minutes with introduction of steam to give a residual moisture content of 60-70%, discharged and classified to give an organic fraction as fines with moisture content 60-70%.

U.S. Pat. No. 4,884,351 (Holloway) discloses an autoclave for the handling of municipal solid waste which is in the form of a cylindrical vessel inclined at about 15° to the horizontal and having frustoconical ends each closed by a hinged hatch. The hatch at the higher end serves as inlet for the waste to be processed and that at the lower end serves as an outlet for processed waste. The autoclave is supported for rotation about its longitudinal axis and has internal flighting angled at about 30° to its axis by which in a forward rotation mode the fighting directs material to the lower end of the autoclave during filling and/or discharge and in a reverse rotation mode material being processed is conveyed upwardly and axially towards the higher end and is mixed and agitated, reverse rotation being during processing of the material. Heating is by introduction of saturated steam via an inlet on the axis of the vessel and at the upper end thereof, the processing temperature being 48-108° C. (120-228° F.) preferably 88-102° C. (190-215° F.) to rupture bags of plastics film but to leave low density plastics materials substantially intact so that they are easily identifiable and separable from other components of the waste.

U.S. Pat. No. 4,974,781 (Placzek) is similar and has as its object the re-pulping of re-pulpable waste material, the water content of the waste typically being 50 wt %. Waste and water is added to a rotary autoclave or so-called "trommel" to give a moisture content of at least 30% of the moisture absorptive components of the waste, 65-75% moisture content being considered an optimum. A working temperature of 100-115° C. (212-240° F.) is considered best for plastics recovery and 115-149° C. is considered best for re-pulping. The autoclave which in use is downwardly inclined at an angle of 4° is provided with lifting blades and directional flighting, a waste inlet at its upper end and a waste outlet at its lower end. The inlet and outlet each have a closure device in the form of a sliding gate valve which is movable axially towards or away from the inlet or the outlet. Steam and water can pass into the autoclave from its lower end via injection piping that extends into and rotates with the autoclave, the piping being connected to a rotary seal on the axis of rotation of the autoclave adjacent the discharge end U.S. Pat. No. 5,445,329 (Anderson) discloses a rotary autoclave mounted to a support frame by trunnions so that the axis of the autoclave can be tilted in either direction so that in one end of its tilting travel its forward end faces downwardly at 45° to the vertical and at the other end of its tilting travel the forward end faces upwardly at 22° to the vertical, these corresponding to loading and discharge states respectively. The vessel is supported in the frame on rotary supports provided with strain gauge based load sensors and by thrust bearings. One end of the autoclave has a door for rotation and discharge of the load, and the other end of the autoclave is provided with an external manifold from which steam can be introduced into the autoclave as it rotates by means of a hollow shaft extending cantilever-wise into the interior of the vessel for a portion of its longitudinal extent, typically 15-25% of the total length of the vessel, the shaft being provided along its length with spaced apart openings or jets through which steam can be introduced into the interior of the autoclave. The strain gauged load sensors are in the form of rollers adjacent opposed ends of the autoclave and are provided for measuring the live load distribution within the vessel. Input from the sensors is used to effect an approximately equal distribution of the material located in the vessel during the treatment operation and to control the angle of inclination of the vessel so that if a sensor associated with a front vessel support detects a load significantly greater than a sensor associated with a rear vessel support, the front end of the vessel is raised so as to cause the material within the vessel to move towards the rear end thereof, this forming part of a so-called "automatic balancing" operation. Nothing is disclosed concerning the use of load sensors in an autoclave having a fixed axis of rotation.

U.S. Pat. No. 5,655,718 (Anderson, divided from U.S. Pat. No. 5,445,329) relates to a method of treating process material, comprising: introducing a first batch of process material to be treated into an interior of a first vessel which has a longitudinal axis; rotating the first vessel about its longitudinal axis; raising the temperature within the interior of the first vessel through the introduction of steam into the interior of the first vessel; introducing a second batch of process material to be treated into an interior of a second vessel; reducing the temperature in the interior of the first vessel while also increasing the temperature in the interior of the second vessel by venting steam from the interior of the first vessel and introducing the vented steam into the interior of the second vessel; continuing rotation of the first vessel after steam in the interior of the first vessel has been vented into the second vessel to facilitate drying of the process material in the first vessel; rotating the second vessel about its longitudinal axis while the first vessel is rotating; and emptying the first batch of process material from the first vessel.

Provision of axial steam inlets at both ends of the vessel is disclosed in U.S. Pat. No. 7,347,391 (Michalek), the vessel being supported so that its direction of tilt can be reversed in order to overcome the problem of load compaction.

Sterilizing waste by heat and pressure, separation of organic matter and fermentation followed by distillation to remove alcohol, centrifugation to remove fats and animal feed components and anaerobic digestion of the effluent to recover methane is disclosed in WO 82/01483 (Holloway), see also WO 2004/041733 (Anderson, Comprehensive Resources).

EP-A-2105414 (Anderson, Sterecycle, divided from a European application corresponding to WO 2004/041733) claims a method of treating waste material, including organic and inorganic materials with the organic materials including starches, cellulose and other carbohydrates, the method comprising: (a) subjecting the waste material to increased temperature, pressure and moisture within an apparatus by introducing steam into the apparatus; (b) increasing the temperature and pressure within the apparatus by an effective amount to cause the steam to reach a saturated state within the apparatus; (c) rapidly reducing the pressure within the apparatus to cause the steam to become superheated; (d) removing the material from the apparatus and passing the material through a screen to separate the material by size (e.g. passing material of size <12 mm); and (e) diluting the biomass obtained from the steam autoclaves with water and subjecting at least a portion of the diluted mixture to anaerobic digestion wherein the portion of the mixture is converted to one or more of a biogas suitable for use as fuel, and a residual sludge. In particular the process involves diluting at least a first portion of the material with water while agitating the resulting diluted mixture a sufficient amount and at an effective temperature to cause cellulose fibres that became twisted and tangled during processing within the apparatus to relax and straighten out or untangle. The specification explains that temperatures of between 126 and 132° C. (260-270° F.) reached within steam autoclaves have been found to enhance the characteristics of cellulose fibres separated from the biomass produced by the autoclaves. They further explain that paper fibre generally includes lignin that binds to the cellulose fibre, hemicellulose, which is the soluble portion of the cellulose, and cellulose, which is very difficult to solubilise unless it is treated with acids, etc. Because the softening point of the lignin is approximately 128° C. (262° F.), the temperatures reached within the steam autoclave causes the lignin that binds to the cellulose fibres to be softened, but the lignin is not heated enough to be crystallized. Low melting point plastics within the biomass form into small beads that are easily separated during subsequent density and size separations so as to not be included with the cellulose fibres used by the paper industry. Anaerobic digestion of the cellulosic material and hydrolysis of the cellulose during the autoclaving step in order to facilitate or improve the anaerobic digestion step is neither disclosed nor suggested.

WO 2009/095693 (Reclaim Resources) discloses a process and apparatus for recycling municipal solid waste comprising subjecting the waste to steam at 150-200° C. After steam treatment, the resultant material is separated into constituent parts and biomass and/or plastics subjected to further treatment which preferably produces bioethanol from the biomass and diesel from the plastics. As an alternative, some or all of the biomass may be gasified in order to produce hydrogen which may in turn be fed to a fuel cell to produce an electrical output. The biodiesel or bioalcohol can also be used to produce electricity. Conducting the autoclave steam treatment under a combination of thermal contact, temperature and pressure conditions such that the cellulosic component becomes significantly hydrolysed within the autoclave is neither disclosed nor suggested.

A further aspect of industrial autoclave design relates to a swing-aside locking door which is acknowledged in Wikipedia to be the most costly and important single piece of hardware in an autoclave. For autoclaves of diameter>four feet (1.2 meters) it is conventional to use a rotating locking ring arrangement or so-called "breech-lock door". U.S. Pat. No. 2,841,308 (Weicker) discloses an arrangement of this type. A circular pressure vessel has a rotatable locking ring mounted on the vessel adjacent a circular aperture thereof, the ring having a series of inwardly facing lugs around its circumference. The door also has a series of outwardly facing lugs around its circumference, the ring lugs cooperating with the door lugs so that as the ring is rotated in a closing direction the door is locked by cam surfaces on the lugs, and as the ring is rotated in a reverse direction the ring and closure lugs move to an unlocked relationship in which the door can move axially away from the aperture. A generally similar arrangement is disclosed in U.S. Pat. No. 2,936,093 (Passalaqua) and in U.S. Pat. No. 3,804,288 (Piegza).

SUMMARY OF THE INVENTION

In some embodiments the present invention permits the processing of unsorted municipal waste, removing the need for separate collections for recyclables, as well as waste from supermarkets, including food waste. Embodiments of the present process also accommodate clinical waste and animal by-products, and allow for the easy separation of clean, sterile recyclables.

Embodiments of the invention permit waste to be processed in an autoclave of simple and mechanically reliable design without the waste forming a compacted mass that subsequently cannot be circulated freely through the autoclave and is therefore resistant to further processing.

In one embodiment the invention provides a method for treating solid waste which comprises: introducing said waste into a rotary autoclave which is downwardly inclined towards its discharge end and has a door at the discharge end; and injecting steam through said door into said autoclave to treat the load.

The invention further provides a method for treating solid waste, comprising steam autoclaving the waste, anaerobically digesting an organic-rich fraction of the autoclaved waste, recovering methane-containing gas from anaerobic digestion, internally combusting the methane-containing gas to generate power and exhaust gas, and generating steam for autoclaving using the exhaust gas.

The invention yet further provides a rotary autoclave for treating solid waste which is downwardly inclined towards its discharge end and has a door at the discharge end, means in said door being provided for injecting steam through said door into said autoclave to treat the load.

A further embodiment of the invention provides a plant for treating solid waste, comprising at least one autoclave for steam treating the waste, at least one anaerobic digestion tank for digesting an organic-rich fraction of the autoclaved waste, a recovery system for recovering methane-containing gas from the or each digestion tank, at least one internal combustion engine for combusting the methane-containing gas and generating power, and a steam generator fed with combustion gas from the internal combustion engine for generating and accumulating steam for supply to said at least one autoclave.

A problem arises in the autoclave treatment of waste in an autoclave in which the axis of rotation is fixed and e.g. inclines forwardly and downwardly, especially waste containing a high proportion of cellulosic material such as paper and card. The result of conveying the waste into the autoclave may be to give rise to a compacted mass of material at the base or forward end of the autoclave as a result of forward rotation of the autoclave during the feeding operation and the action of screw flights within the autoclave. The resulting compacted mass may be difficult to disperse during subsequent vacuum or steam processing merely on rotation of the autoclave in a direction opposite to the direction of rotation during load introduction The compacted mass may then not be effectively be treated during the vacuum and steam treatment phases of the autoclaving cycle and may in extreme cases require manual removal at the end of such cycle. Even occasional occurrences of persistent compacted mass at the end of autoclaving may give rise to significant operational difficulties. It is therefore desirable to provide a method for externally monitoring load behaviour during the vacuum and/or steam phases of treatment to ensure that the load has not remained as a compacted mass and is circulating between the ends of the autoclave.

Accordingly yet further embodiment of the invention provides a method of treating waste material in a rotary autoclave, which comprises: loading the waste material into a top opening of the autoclave whilst rotating the autoclave in a first direction in which screw flights within the autoclave convey the waste forwardly along a downwardly inclined body of the autoclave towards a base of the autoclave; rotating the autoclave in a second direction opposite to the first direction so as to establish a circulation of the loaded material between the upper and lower ends of the autoclave to facilitate vacuum and/or steam treatment thereof; and monitoring the load imparted by the autoclave adjacent upper and lower ends thereof during the reverse rotation, increase of the load adjacent the upper end of the autoclave providing an indication of effective load circulation. If the load is not circulating as desired, remedial action may then be taken e.g. adding water and/or steam from the base of the autoclave, adding water and/or steam at the top of the autoclave or both. Programmable logic control (PLC) can be used to dynamically modify the control parameters of the process to ensure that the waste is thoroughly mobilised within the autoclave and of uniform temperature throughout.

Hydrolysis is the controlling step in the anaerobic digestion (AD) of organic solids. The process of hydrolysis requires weeks to complete in a traditional AD process. A major disadvantage for AD of solid wastes is that the process requires large reactor capacities. Through an autoclave pretreatment, the majority of organic solids with an appropriate combination of contact, processing temperature and processing time can be thermally hydrolysed and liquidised. Hence, the retention time for the following AD process can be significantly shortened and the digester tank size can be significantly reduced. Furthermore, the combination of thermal and mechanical degradation induced by the autoclave has the effect of vastly increasing the amount of organic material that can be digested by AD.

Another major drawback for traditional AD is the ammonia toxicity to the anaerobic micro-organisms associated with treating high protein content wastes. Thermal denaturation and/or hydrolysis of protein in an autoclave alleviate the inhibition of bacterial activity by ammonia build-up. High protein waste includes slaughterhouse waste and animal by-product wastes as well as food waste e.g. from supermarkets and catering establishments. A major problem in slaughterhouse waste is the treatment of blood, and it is believed that slaughterhouse blood waste can be treated in an autoclave of the present kind and then passed on for anaerobic fermentation without unacceptable ammonia build-up. A further major weakness for AD is that the process has limited tolerance to shock loadings mainly caused by uneven qualities of feedstock. Autoclaving produces a thoroughly homogenised feedstock for the AD which significantly reduces the risks from shock loadings.

A further problem with which the invention is concerned is the provision of a door mechanism for an autoclave for treating municipal or other solid waste, in which the locking and release mechanism is resistant to becoming jammed or clogged e.g. with ribbon or tape or with pieces of fabric forming part of the waste being treated, and which is easy to clean e.g. with a pressure hose.

The invention further provides a door assembly for an autoclave comprising a castellated door and an autoclave rim provided with a locking ring, wherein the locking ring has lock blocks of inwardly facing U-configuration between which the door castellations can pass when the ring is in a release position and which as the ring is rotated to a closure position traps the door castellations against a protruding flange of the rim, the rim flange running within an inner leg of the lock blocks and the door castellations being received behind an outer leg of the lock blocks as the ring is rotated towards its closure position.

In embodiments, the locking ring comprises inner and outer annular plates between which the lock blocks are secured, the inner annular plate in embodiment carrying roller bearings configured to run on a track on the autoclave rim for rotatably supporting the locking ring and the inner leg of the lock blocks locating within a groove of the autoclave rim. Also in embodiments the outer legs of the lock blocks and the castellations of the door have opposing wedge faces configured to cam the door towards the rim as the ring is rotated towards its closure position and the outer legs of the lock blocks are faced with a low friction material for contact with the rim castellations. The inner legs of the lock blocks may also be faced with a low friction material for contact with the protruding flange. Facings of low friction material may also be removably attached to the outer and inner legs. The low friction material may be PTFE in sheet or block form and may be attached by means of screws or bolts.

For self-centering of the door as it is closed, the rim may be formed with an outwardly protuberant frustoconical surface which opposes a corresponding surface of the door as the door is closed to align the door with the autoclave rim and the door may be mounted to the autoclave for linear travel when closer to the autoclave and for swinging travel when further from the autoclave.

The door may have a steam plenum chamber and one-way devices by which the steam can pass into the autoclave but autoclave contents cannot pass into the plenum chamber, where there is a plurality of such devices providing parallel paths from the plenum chamber into the interior of the autoclave. The cross-sectional area of the path or paths from the plenum chamber into the autoclave defined by said at least one one-way device may be equal to or greater than the area of an inlet for injected steam into the plenum chamber in order to avoid excessive pressure drop across the one-way devices. As previously explained, the one-way devices may be sintered metal discs leading from the plenum chamber into the autoclave, or they may be mushroom or poppet valves or other one-way valves leading from the plenum chamber into the autoclave. The rim may have inner and outer annular gaskets provided with tongues facing away from between the gaskets to resist pressure and vacuum, the tongues becoming compressed as the door is closed and deformed into recesses in the rim.

In a further aspect the invention provides a door assembly for an autoclave comprising a castellated door and an autoclave rim provided with a locking ring, the rim having inner and outer annular gaskets provided with tongues facing away from between the gaskets to resist pressure and vacuum, the tongues becoming compressed as the door is closed and deformed into recesses in the rim.

The above mentioned door assembly is particularly useful for the discharge door of a downwardly inclined autoclave, but it may also be provided at the upper or inlet end thereof. It will also be understood that references to the supply of steam also apply mutatis mutandis to the application of vacuum, since both steam and vacuum are used in the processing of municipal or other solid waste.

Other features of the invention are defined in the accompanying claims to which attention is directed. The features in the dependent claims of each independent claim are in general applicable mutatis mutandis in combination with the features of other dependent and independent claims.

BRIEF DESCRIPTION OF THE DRAWINGS

How the invention may be put into effect will now be described, by way of example only, with reference to the accompanying drawings, in which.

DETAILED DESCRIPTION OF PREFERRED EMBODIMENTS

Effects of Autoclaving MSW

Figure 1:
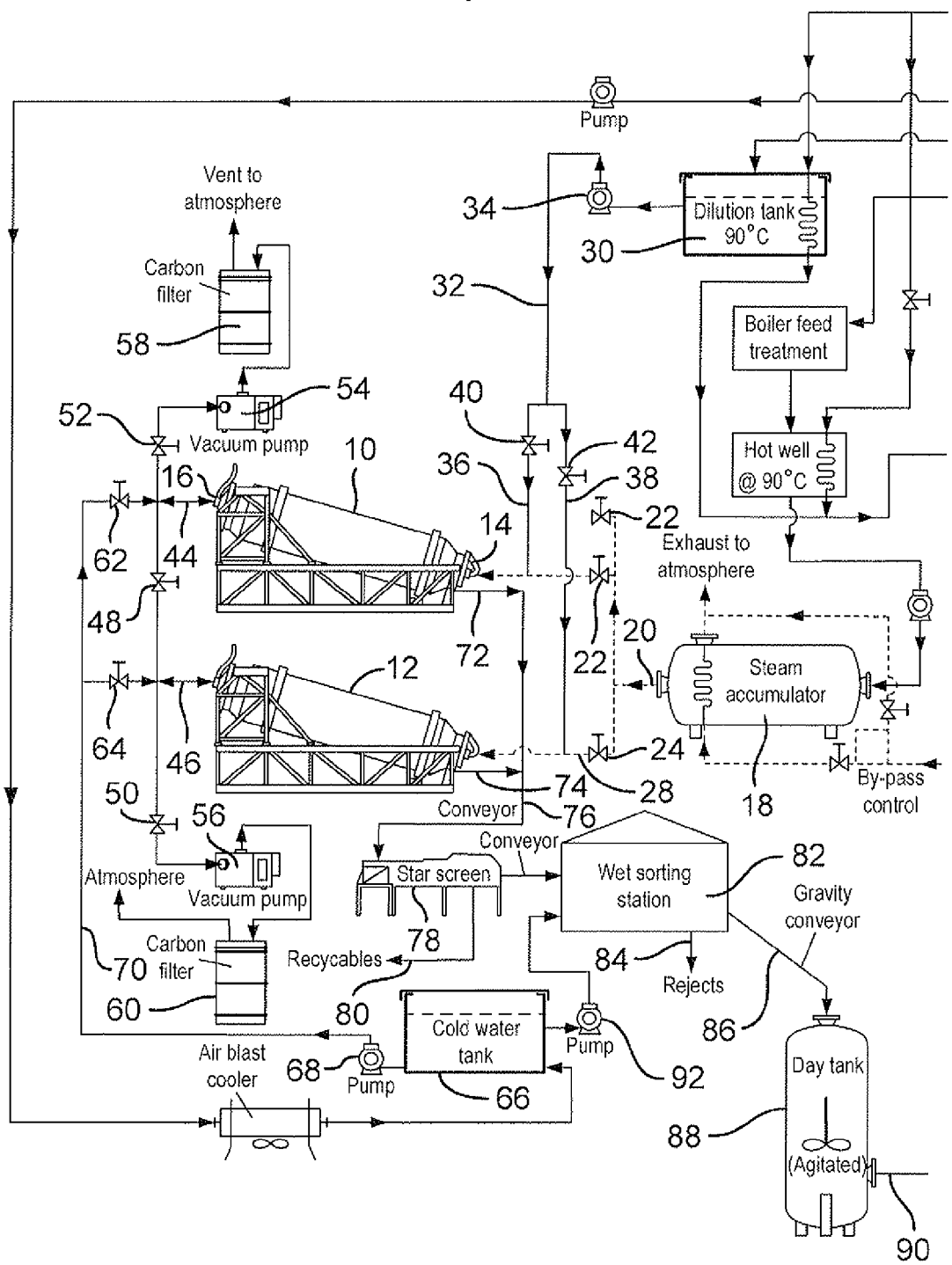
FIG. 1 shows diagrammatically autoclaving and sorting portions of a plant for treating municipal solid waste.

There is a benefit in putting MSW through an autoclave, as the resulting material of high organic fraction and high water content can be subjected to anaerobic digestion which breaks down organic matter to produce methane gas, which can be used to drive a generator to produce 'green' electricity. Because the electricity is produced from a renewable source, in UK it currently attracts extra allowances under the Renewable Obligation Credits (ROCs) scheme as of December '09, making it worth around 15 p per kWhr, and most of this electricity can be supplied to the National Grid. The process of generating electricity also generates waste heat, which is used to produce the steam for the autoclaves via waste heat recovery boilers. In addition, surplus heat can be used for other purposes. After removal of metals and plastics, cellulose floc can either be removed or as in the disclosed embodiment left in the mixture that goes into the anaerobic digester.

The bio-gas that comes off the digester is used to generate electricity. The generator is only about 35% efficient, and the rest of the energy is released as heat, of which part is used to generate steam for the autoclave. The resulting sludge from the digester can be burnt as bio-mass, put into a gasifier to produce 'syngas', composted or even formed into a building material.

Processing the organic materials in the autoclave results in them breaking down much more quickly in the anaerobic digester; the lignin (a complex chemical compound) in the organic matter starts to break down, so more gas is produced more quickly. The gas yield can be double that form non-autoclaved waste; furthermore, the peak gas flow rate can be produced in four days rather than four weeks.

The EU landfill directive calls for the amount of organic waste sent to be halved by 2013, and this requirement is backed up by an escalating tax regime. EU Landfill Tax is rising at a rate of £8 per tonne per year (it is currently at £40 per tonne) and is expected to reach £70 per tonne within 5 years. Including tax, the cost of disposing of waste to landfill is currently around £60 a tonne. The social climate is also in favour of sustainable waste solutions; there is a general desire to show more concern for the environment, but at the same time, people do not like the idea of being fined for putting out to much rubbish or mixing up recyclable products. Embodiments of the present process and apparatus not only remove the need to separate out different types of waste; they can also offer local authorities the chance to profit from their waste, rather than paying to get rid of it.

Autoclaving at an appropriate temperature and for an appropriate time can help to avoid excessive concentrations of volatile fatty acid (VFA) building up, which is an indication that anaerobic digestion is failing. Anaerobic microorganisms used in anaerobic digestion are a mixed culture. They mainly contain three groups of bacteria: hydrolytic enzyme bacteria, acidogenic and acetogenic bacteria, and methanogenic bacteria. The hydrolytic enzyme group is responsible for hydrolysing long chain organic compounds into soluble small molecular substrates which can then be converted to VFA's by the acidogenic bacteria and eventually to acetic acid by the acetogenic bacteria. Finally the methanogenic bacteria will convert acetic acid to biogas, which mainly contains methane and carbon dioxide. When an anaerobic digester is reasonably loaded, these groups of bacteria are working in harmony. Once the loading increases, each group of bacteria will develop to reach a new balance to cope with the change of feeding rate. When the digester is overloaded, however, the metabolic balance of the different groups of anaerobic bacteria will be destroyed. The enzyme group becomes overdeveloped and development of the methanogenic bacteria will become reduced. However, the acidogenic/acetogenic bacteria are a very strong group and can carry on fast metabolism under tough circumstances as long as the temperature is maintained at a suitable level. Under these conditions a build-up of VFA's in the digester can be observed and the process failure becomes inevitable.

Autoclave pre-treatment can bring about cellular disruption which can facilitate subsequent anaerobic digestion. It can hydrolyse the majority of the cellulosic material in the waste which can reduce the need for bacterial enzyme hydrolysis in a downstream anaerobic digestion process. When the digester is fed with autoclaved waste, the mechanism of the metabolism of the anaerobic bacteria will be automatically emphasised on the development of methanogen. Therefore more biogas will be produced by the autoclaved materials than non-autoclaved at the same loading rates. In other words, to reach the same gas production rate, higher loading rates can be applied on the autoclaved waste than on the non-autoclaved waste. This means for treating waste streams with the same solids concentrations shorter retention time can be used on the autoclaved waste. Hence the digester volume can be reduced.

Autoclave Features

In embodiments of the invention, running reliability of a rotary autoclave for MSW can be improved and the range of materials that can be effectively treated is improved by employing an autoclave having a fixed downwardly facing attitude and injecting steam through a port in a bottom discharge door of the autoclave. In particular a fixed attitude facilitates making the autoclave body or tunnel of material of adequate thickness not only to resist internal steam pressure but also to continue to do so if there is corrosion or erosion as a result of processing wet loads of MSW. For example in a commercial-scale autoclave of diameter e.g. 3-5 meters and length 10-20 meters the autoclave body or tunnel may be formed of steel plate of significantly greater than the 9 mm steel plate as in other proposals e.g. 12-25 mm, the precise thickness depending e.g. on the dimensions of the autoclave or autoclaves proposed to be used. The autoclave may face forwardly and downwardly at an angle of 5-20°, e.g. 10-15°, conveniently about 15°.

The door may be hinged to a support frame of said autoclave for rotational movement between one position in which a discharge opening of the autoclave is revealed and another position in which the discharge opening is closed. Advantageously the door carries a rotary coupling for receiving steam from a supply pipe as the autoclave is rotated. A plenum chamber for steam in may be provided said door. Steam may be injected into the interior of the autoclave through a plurality of one-way devices providing parallel paths from the plenum chamber into the interior of the autoclave, thereby facilitating steam injection without undue pressure drop across the devices. For that purpose the cross-sectional area of the path or paths from the plenum chamber into the autoclave defined by said at least one one-way device may be equal to or greater than the area of an inlet for injected steam into the plenum chamber. Injecting the steam into the autoclave may be through at least one porous sintered metal disc leading from the plenum chamber into the autoclave or it may be through at least one mushroom or poppet valve or other one-way valve leading from the plenum chamber into the autoclave. The autoclave may also have an inlet door for waste at its upper end, and an axially located inlet in said door for water to be sprayed into the autoclave to condense steam therein. Water and steam leaving the plenum chamber pass directly into the internal space of the autoclave, and not through distribution pipes extending along that space. The door may be supported for hinged movement between open positions and a position spaced from and axially aligned with the discharge opening and is supported for translational movement between the spaced axially aligned position and the position in which the discharge opening is covered.

The method of treatment of the solid waste may include injecting steam from a steam accumulator having a capacity for a body of steam at a temperature and pressure effective to heat and fully penetrate the load and may also include injecting recycled steam from a second autoclave which has substantially completed its treatment cycle.

In an embodiment the autoclave has generally helical internal flights, and it is rotated during steam injection in a direction such that the flights lift the waste from the discharge end into the body of the autoclave. Process control may include monitoring load at upper and lower ends of the autoclave while the flights are lifting the waste from the lower end, equalization of the load at the upper and lower ends compared to the loads at the end of waste introduction indicating that lifting is taking place. Process control may further include monitoring pressure at upper and lower ends of the autoclave, substantial equality of pressure indicating that the steam has fully penetrated the load. In embodiments of the present process the processing time is considered to have started when the load has become fully penetrated by the steam. In a further feature liquid water is introduced into the autoclave as the load is introduced, the water advantageously being near boiling and introduced in an amount of 25-100% based on the weight of the introduced load, e.g. 25-50 wt % based on the weight of the introduced load. A yet further feature comprises spraying water into the autoclave after steam injection and completion of the processing cycle in order to bring about steam condensation, the amount of water sprayed into the autoclave typically being 25-50 wt % of the weight of the waste at the start of processing.

The present system uses an inclined tunnel-shaped rotating-drum autoclave that has an internal Archimedes screw welded to the vessel. This is rotated in one direction during loading to facilitate the loading of the autoclave, and rotated in the other direction during operation to break up the waste and ensure that the load is evenly processed. Once the vessel is fully loaded, all the air is extracted to create a vacuum. This vacuum bursts open any packaging or unopened containers and also helps to ensure that, when the steam is let into the vessel, it completely penetrates the load. When the chamber has reached its optimal operating conditions (160° C. and several atmospheres pressure), the mixture is allowed to cook for about 40 min.

In embodiments three types of autoclave (all scaled from the same basic design) may be supplied in pairs to allow the steam to be recycled from one autoclave to the other to save energy. A relatively small autoclave has in an embodiment a seven-tonne capacity and is primarily aimed at processing food waste. 15-Tonne and 30-tonne vessels are suitable for local-authorities and large scale treatment of municipal standard waste. A pair of the 30-tonne autoclaves can process around 600 tonnes a day (200,000 tonnes a year), which equates to the waste disposal needs of about 400,000 people. Based on a 100 ktpa plant and recognised prices for the components of a standard tonne of waste from the borough of Tower Hamlets in London, this will produce annually over £3.5 million worth of fibrous floc, plus over £1 million worth of recyclable material, and generate £6 million of gate fees for a commercial operator (or save the same amount for a local authority). If the organic matter, including the cellulose floc, is instead processed in anaerobic digesters and used to produce electricity, this will generate an additional £2.5 million worth of 'green' electricity and cover all the heat and energy needs of a plant.

In FIG. 1, alternately operating autoclaves 10, 12 are mounted in support frames for rotation about their longitudinal axes, slope downwardly at about 15° and are provided at opposed ends with lower and upper doors 14, 16. The autoclaves may, for example, each process a 15 tonne load, and be of length typically 13 m and diameter 3.33 m. Water which is preferably heated to near boiling e.g. 90° C. can be pumped from dilution tank 30 via line 32 by pump 34 and then via branch line 36 or 38 under the control of valve 40, 42 into the autoclave, via lower end door 14. For each processing cycle, 7.5 tonnes of water may be added at the start of the cycle through the lower door 14 in this way. Steam from accumulator 18 can pass via outlet 20 through lower end door 14 into one or other autoclave when control valve 22 or 24 is open to permit steam to pass via branch pipe 26 or 28 into a selected autoclave 10 or 12. All fresh steam is introduced through lower door 14, and at the start of the cycle. Typically about 3.25 tonnes of steam is injected via the bottom connection and turns into condensate. At any given time either water or steam is introduced, so that valves 40, 42 are closed when one of valves 22, 24 is open and valves 22, 24 are closed when one of valves 22, 24 is open. When required, the pressure within either autoclave 10, 12 can be reduced by respective vacuum pumps 54, 46, valves 62, 64 and 48 then being closed, and valve 48 or 50 being open depending on which vacuum pump is working Gas pumped from each autoclave by vacuum pumps 54, 56 is filtered by carbon filter 58 or 60 and vented to atmosphere. The autoclaves 10, 12 may work at 130-170° C., a temperature of 160° C. and a pressure of about 6 bar being considered optimum.

At the end of a process cycle, steam can be recycled from one of the autoclaves which is ending its processing cycle e.g. 10 to the other autoclave e.g. 12 which is beginning its processing cycle on opening valve 48, valves 50, 52, 62, 64 being closed. Recycled steam enters through top door 16. During depressurisation within an autoclave condensate is re-evaporated and transferred to the other autoclave via valve 48, the other autoclave then having already been loaded and evacuated by the vacuum pumps. The recycled steam preheats the second autoclave before fresh steam is admitted from the steam accumulator (18) and this minimises the quantity of fresh steam required. The remaining steam in the autoclave 10 or 12 at the end of its cycle can then be condensed by adding cold water from tank 66 using pump 68 and line 70, valve 62 or 64 being opened and valves 48, 50 and 52 being closed. About 15 tonnes of water may be added at the end of the processing cycle, condensing residual steam and cooling the waste to about 70° C.

Figure 4:
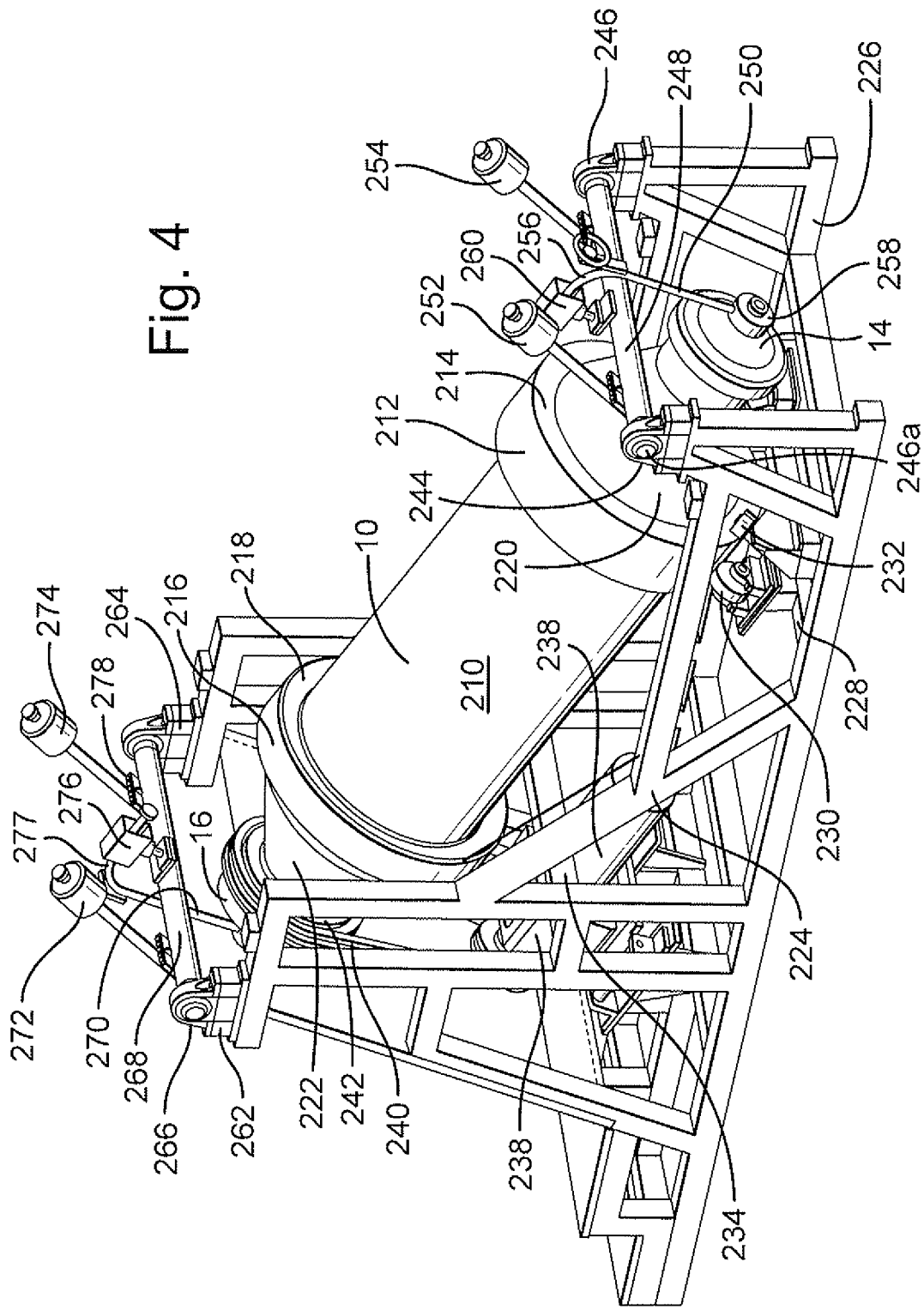
FIG. 4 is a simplified oblique view from a lower end thereof of an autoclave and support structure, and being a pilot version of one of the autoclaves of the treatment plant of FIG. 1, upper and lower doors being shown in their closed positions.

A pilot-scale autoclave for demonstrating the construction and operation of the autoclaves 10, 12 is shown in FIG. 4. The autoclave 10 has a cylindrical body sloping downwards as shown at about 15° and having a central cylindrical region 210 bounded at its upper and lower ends by welded-on lower and upper support rings having cylindrical side surfaces 212, 216 and lower side surfaces 214, 218. On the further sides of the support rings the body has lower and upper tapered e.g. frustoconical or dished regions 220, 222 which are removably closed by the lower and upper doors 14, 16. The autoclave is supported in a fixed attitude relative to the horizontal in a framework having first and second sides 224, 226 joined by cross-members e.g. 228, 234. At its lower the autoclave body is supported for rotation in the framework by support wheels 230 carried by cross-members 228 which run on the side surface 212 of the lower support ring and by thrust rollers 232 which run on the lower side surface 214 of the lower support ring and provide a reaction for the sideways component of the load of the autoclave body and its contents (i.e. load in a direction longitudinally of the autoclave body). At its upper end the autoclave body is supported for rotation by support wheels 234 which run on the side surface 216 of the upper support ring. Drive motor 238 carried by the frame is operable to rotate the autoclave body in either direction via drive chain or belt 240 and driven wheel 242.

The pivot mechanism for lower door 14 is as follows. At a location spaced upwards from the axis of the autoclave the support frame has fixing brackets 244, 246 for hinge pin 246 which carries hinge sleeve 248. The door 14 is attached to the sleeve 248 by arm 250 and is balanced by counterweights 252, 254. Fluid delivery line 256 passes along arm 250 to pressure-tight rotary pipe coupling 258 where the radially incoming steam or water is supplied to the door 14 through which it passes axially inwards and upwards into the autoclave. Flow through line 256 is controlled by valve 260, and there is an end coupling for steam and water supply pipes. The upper door 16 is similarly supported by brackets 262, 264 on the frame that support hinge pin 266 and hinge sleeve 268. Similarly to the door 14, the door 16 is mounted to the hinge sleeve by arm 270 and is counter-weighted by weights 272, 274, a steam and water supply line 277 leading to control valve 276 and then to connector 278 which is visible in this view and which provides a connection to steam and water supply lines.

Figure 5:
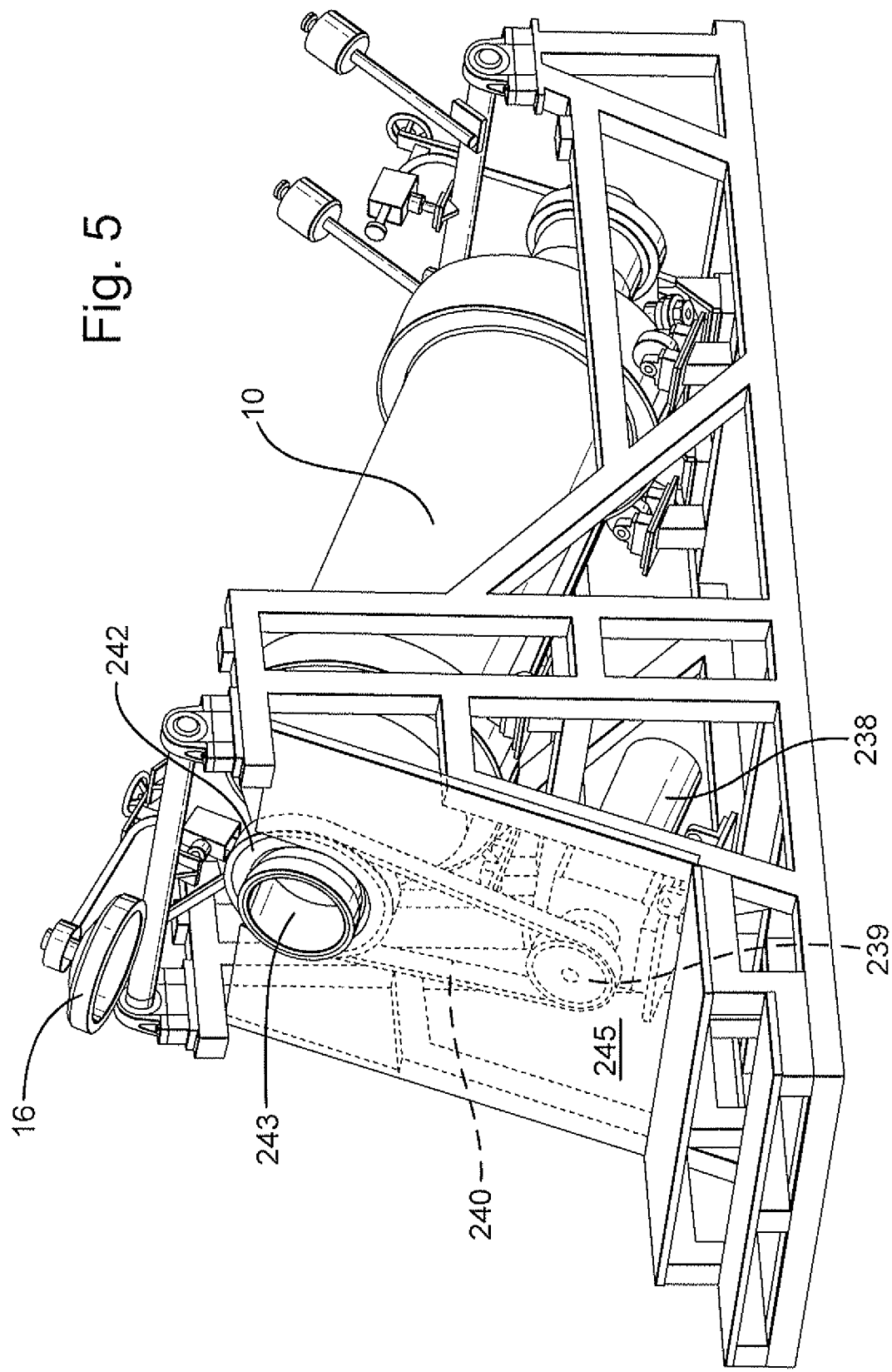
FIG. 5 is an oblique view of the autoclave of FIG. 4 from its upper end, an upper door being shown in its open position.
Figure 6:
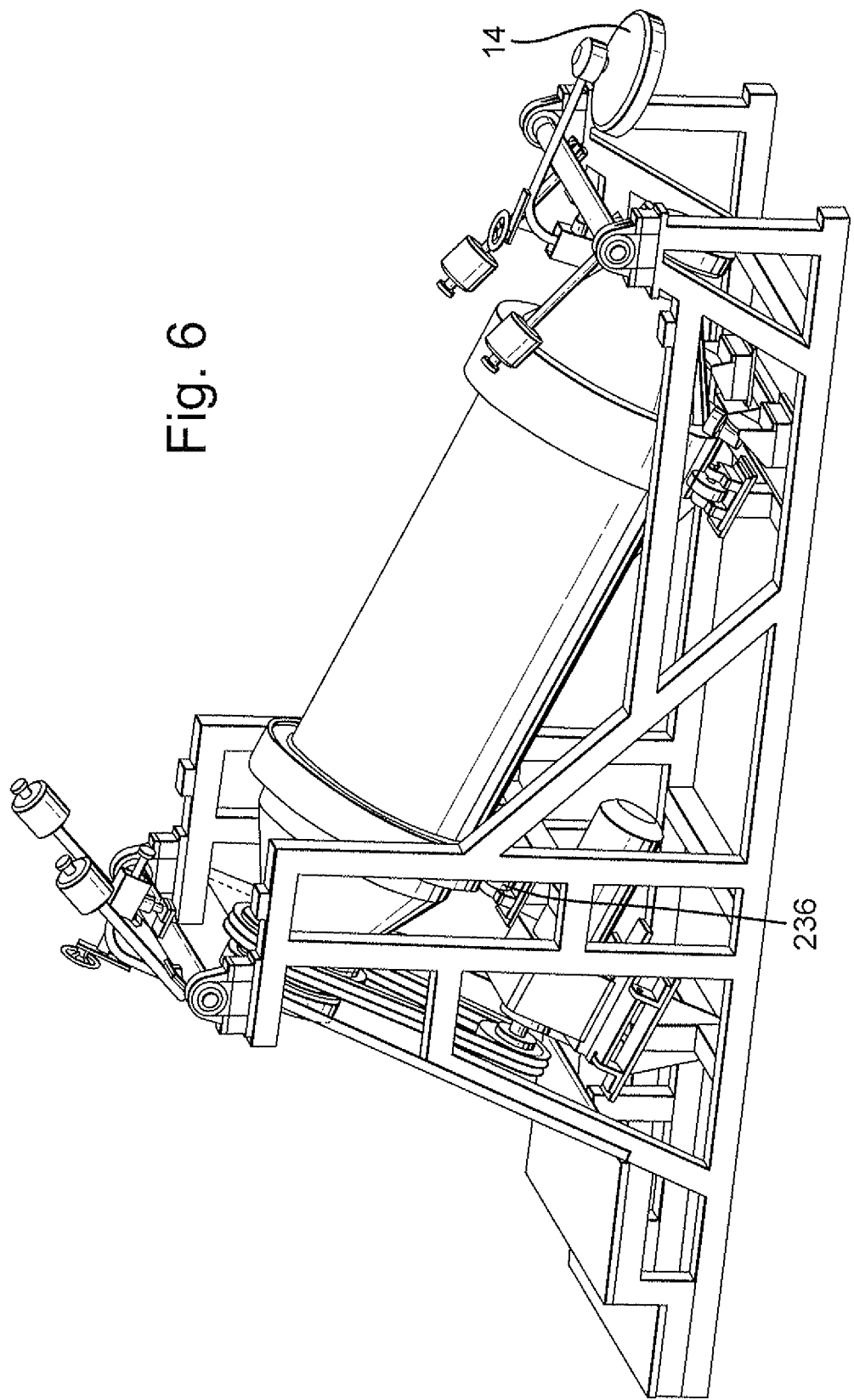
FIG. 6 is a slightly oblique side view of the autoclave showing the lower door in its open position.
Figure 7:
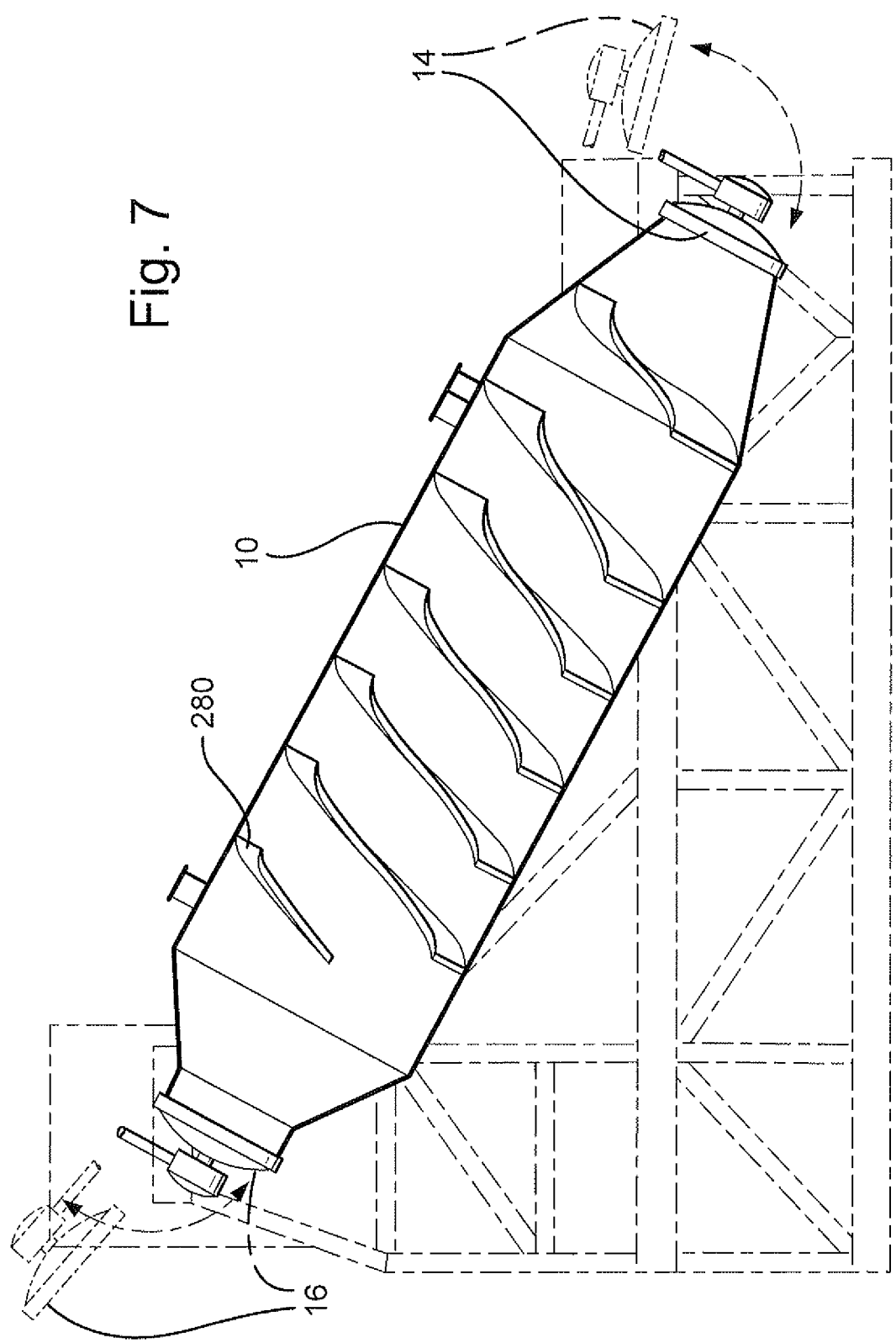
FIG. 7 is a further side view of the autoclave with both upper and lower doors open and with the autoclave viewed in longitudinal vertical section to reveal its internal flights.

FIG. 5 is an oblique view of the autoclave from its upper end with the door 16 in its open position to reveal waste inlet 243. Drive wheel 239 on the shaft of motor 238 is also apparent. A safety plate 245 of metal or plastic covers the motor and drive belt 240 to reduce the risk of injury to operators of the autoclave. In FIG. 6 the lower door 14 is shown in its open position for discharge of treated waste. In FIG. 7 the autoclave is shown in side view in longitudinal vertical section to reveal single start or two start internal helical flights 280 thereof defining an Archimedean screw, the doors 14, 16 being shown in their open positions.

Figure 8:
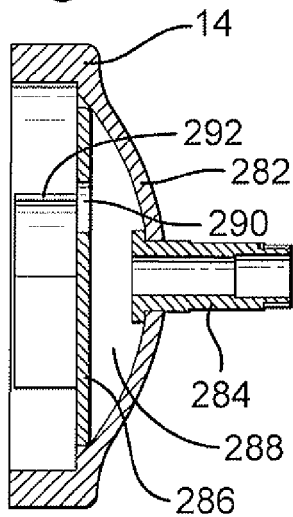
FIGS. 8 and 9 are respectively a vertical sectional view and a front view of a lower door forming part of the autoclave of FIG. 4, and FIGS. 10 and 11 are views of a retaining washer for fitting to the door of FIGS. 8 and 9.
Figure 9:
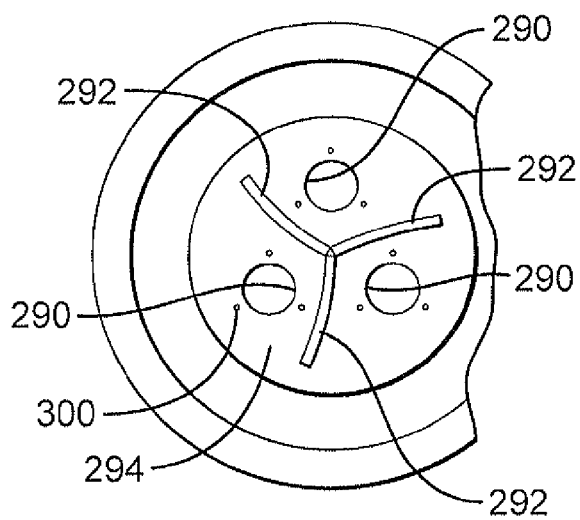
Figure 10:
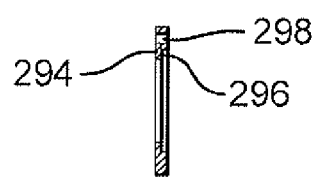

FIGS. 8 and 9 are sectional and front views of the door 14. The door body comprises a front dished region 282 and an upstanding rearwardly projecting flange region 280 which fits over and assists in sealing with the lower opening of the autoclave body from which treated waste is discharged. A stub pipe 284 passes axially through dished region 282 for leading water and steam from rotary connector 258 into the autoclave. Plate 286 is welded or otherwise secured to the door body at a small spacing rearwardly of the dished region 282 to define therewith a plenum chamber 288 having outlets 290, in this embodiment three in number. Each outlet 290 is fitted with a structure defining a one-way valve such that water and steam can pass from plenum chamber 288 into the body of the autoclave, but autoclave contents substantially cannot pass into the plenum chamber and in particular fines from the waste cannot pass to the rotary joint 258. In this embodiment the one-way valves are provided by discs of sintered particles of stainless steel in which the sintered particles are of size about 60 μm. In a full-scale autoclave the porous stainless steel discs may also be used, or may be replaced by one-way valves e.g. poppet valves. In the present embodiment the discs (in this embodiment diameter 60 mm, thickness 3 mm) have the advantage that that act as one way valves but have no moving parts. The discs are secured to the rear face of plate 286 by retaining washers 294 which are rebated at 296 on their forward faces to receive and retain the stainless steel discs and are formed with bolt holes 298 to permit the washers and the steel discs to be attached to the plate 286 by bolts passed through holes 298 and received in threaded holes 300 in the plate 286. Fins 292 tend to space the load slightly from the discs or other valve structures and thereby facilitating the start of water or steam introduction into the autoclave. It will be noted that the door has no structure that enters substantially into the interior space of the autoclave, and that it may be hingedly moved aside from the bottom discharge opening of the autoclave for load discharge without any part of the door obstructing this movement.

The construction of the upper door 16 is generally similar to that of the door 14, and it may incorporate porous stainless steel discs or poppet valves. However, these may not be necessary and a simple metal mesh closing the three openings in the plenum plate may suffice.

Figure 12:
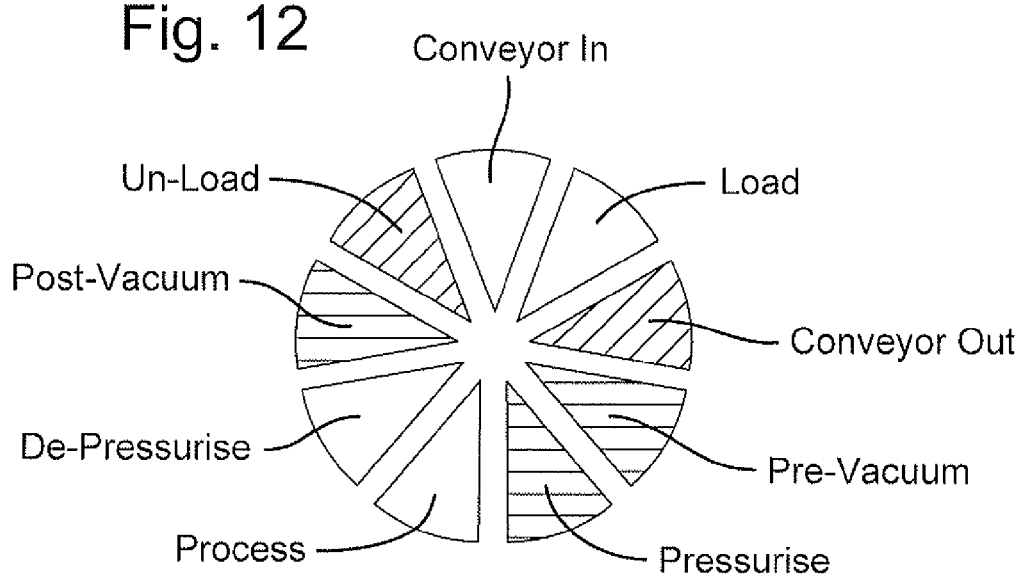
FIG. 12 is a timing chart for batch processing using a single autoclave as shown in FIGS. 4-7.

FIG. 12 shows a timing chart for operation of a single autoclave as shown in FIGS. 4-7. At the start of processing upper door 16 is opened and a conveyor for MSW material is introduced into upper opening 243, this occupying some 2 minutes of processing time. The autoclave is then rotated in a forward direction to permit loading to take place, the internal flights 280 forwarding the load towards the lower door 14. At the same time any water needed at the start of processing may be introduced through the upper door 16. If the load comprises food waste only, it may not be necessary to add water since the putrescible content of food waste already has a water content of circa 80%. If paper or card is present in the load, then water is desirably added to prevent undue densification of the load that would interfere with subsequent processing. The amount of water added will depend on cellulosic content and should be in an amount that is effective to maintain mobility of the load during subsequent processing and to soften the lignin content of the load. It may comprise 25 wt % based on the weight of the MSW, more usually about 50 wt % and if the cellulosic content is high 100% or above, the 50 wt % figure being typical. The load volume at initial filling should be <75% of the internal volume of the autoclave.

On completion of loading, door 16 is closed and the pressure in the autoclave is reduced using a vacuum pump to remove air and volatiles from the autoclave, the discharged gas being filtered by means of a carbon filter and vented to atmosphere. During venting the autoclave is rotated in the reverse direction so that the load is continuously circulated towards the upper door 16 and then returns under gravity. Support rollers 230 and 236 include strain-gauge based load cells by which the load in the autoclave at various stages can be checked. These load cells, in particular are employed during this stage and during subsequent hot processing of the load to check for a relatively even load distribution between upper and lower parts of the autoclave, showing that the load has not remained compacted at the lower end of the autoclave.

On completion of the vacuum pre-treatment stage which may last about 15 minutes, steam and optionally further water are introduced through door 14 to raise the internal temperature of the autoclave e.g. to about 160° and the pressure to about 6 bar. Pressurization of the autoclave may take some minutes, substantial quantities of the introduced steam condensing in the initially cold load as indicated above to increase the water content thereof. Circulation of the load through the autoclave by reverse rotation is continued, and even load distribution continues to be monitored to check that the load has not compacted and remains at the bottom of the autoclave. Penetration of the steam into and through the load is gradual, and pressure is monitored at both ends of the autoclave, rise of pressure at the upper end of the autoclave to or close to the rated processing temperature ~160° C. indicating that the pressurization step is complete. By introducing steam from the lower end and monitoring pressure (or temperature) at the upper end of the autoclave, it is possible to ensure that the whole of the load has been penetrated by the steam. Processing at the working temperature and pressure is then carried out for a period of time effective to break down the load and in particular any paper and cellulosic content of the load and water being added from below or above the load via door 14 and/or 16 as desired. It will be appreciated that the load material shrinks substantially during processing as plastics items are softened and board structures collapse.

On completion of the processing step the autoclave is abruptly de-pressurised and water is injected through the upper door 16 and sprayed into the interior of the autoclave to collapse the steam in the load and avoid a steam plume. Abrupt de-pressurising is advantageous since it disrupts any residual cell structure in the load material and makes the load contents more accessible to the microbes in the subsequent anaerobic digestion step. As previously noted, a considerable volume of water may need to be added for this purpose, this being possible because of the load shrinkage during the thermal processing step, and the volume of added water typically being ~50 wt % of the mass of the waste being treated. De-pressurisation may take 10 minutes. In a dual autoclave installation, the steam from the working autoclave will, of course, be recycled to the start-up autoclave as previously described. The autoclave is again subjected to vacuum treatment, this stage lasting for some minutes. The direction of rotation of the autoclave is then again reversed, the lower door 14 is opened and the load is discharged, some minutes being allowed for this operation. It will be appreciated that the load has now been diluted with large amounts of water so that at the end of processing the combined collapsed load and added water approximately 50% fills the autoclave, but this is not a problem because the feedstock for the subsequent AD digestion stage is desirably a dilute aqueous slurry.

Thermocouples and load cells for the autoclave may provide inputs for a microcontroller or computer with appropriate stored instructions e.g. to execute the following start up logic for one of a pair of autoclaves with steam recycling:
1. Record load cell readings and measure differential.
2. Inject set amount of water into the autoclave through the open door.
3. Record load cell readings and measure differential.
4. Add known weight of waste with slow forward rotation.
5. Record load cell readings and measure differential.
6. Stop rotation, close door and confirm closed condition.
7. Record load cell readings and measure differential.
8. Start rotation in reverse direction and start vacuum pump.
9. Record load cell readings and measure differential.
10. When pressure has fallen to a preset level (P1) stop the vacuum pump and start steam recycling via the top door. After pressure has stabilised, start fresh steam injection via the lower door.
11. When pressure at the top door has risen to a preset level (P2) stop steam injection.
12. With rotation on, record the upper and lower load cell readings.
13. Turn rotation off and leave for a set time before taking a further set of load cell readings.
14. Calculate the average change in weight for both load cell positions.
15. Restart rotation in reverse direction and, after a set time, take a further set of load cell readings.
16. Calculate the average change in weight for both load cell positions.
17. Calculate an average of the averages calculated in 10 and 13. This is the weight movement induced by rotation. This will be compared to a set value which is the criterion for successful movement.
18. IF the average change exceeds the set value then the steam supply is turned on again and the pressure allowed to rise to the main set point (P3).
19. IF the average change is less than the set value then a set amount of water will be injected through the bottom door and the process returns to step 7.
20. If this is still unsuccessful in mobilising the load, this loop can be repeated.
21. If it is unsuccessful after a specified number of loops, the process will be put on hold and operator intervention will be requested.

Anaerobic Digestion

The invention may further comprise supplying an organic-rich fraction of processed waste from the autoclave to an anaerobic digester, and recovering a methane-rich gas there from. The anaerobic digester advantageously operates under mesophilic or thermophilic conditions. Methane-rich gas may be supplied to at least one internal combustion engine (e.g. based on reciprocating pistons or a turbine) for generation of power and exhaust gas, and generating steam for said autoclave using the exhaust gas from said internal combustion engine. Recovered jacket water may be used for heating water be supplied to the autoclave and also water to be supplied to a steam generator of the autoclave or anaerobic digestion system. Recovered jacket water may also or independently be used to conduct anaerobic digestion at an elevated temperature e.g. to maintain mesophilic or thermophilic conditions Referring again to FIG. 1, on completion of the processing cycle, waste stream 72 or 74 passes via conveyor 76 to star screen 78. Recyclables pass from the primary screen at 80 and it is expected that about 3.5 tonnes per cycle of recyclables will be removed in this way. The digestible organic fraction passes to wet sorting station 82 where it is combined with cold water pumped via pump 92 for cleaning and cooling, about 12 tonnes of water being added to cool the waste to about 50° C. The waste then passed via gravity conveyor 86 to stirred day tank 88 which can accommodate material from several autoclave batches each amounting including condensate and added water to about 54.25 tonnes. In order to accommodate four autoclave loads, the holding tank will need to be of size about 250 m$^3$, and its contents are stirred as shown to maintain the organic materials in suspension.

Figure 2:
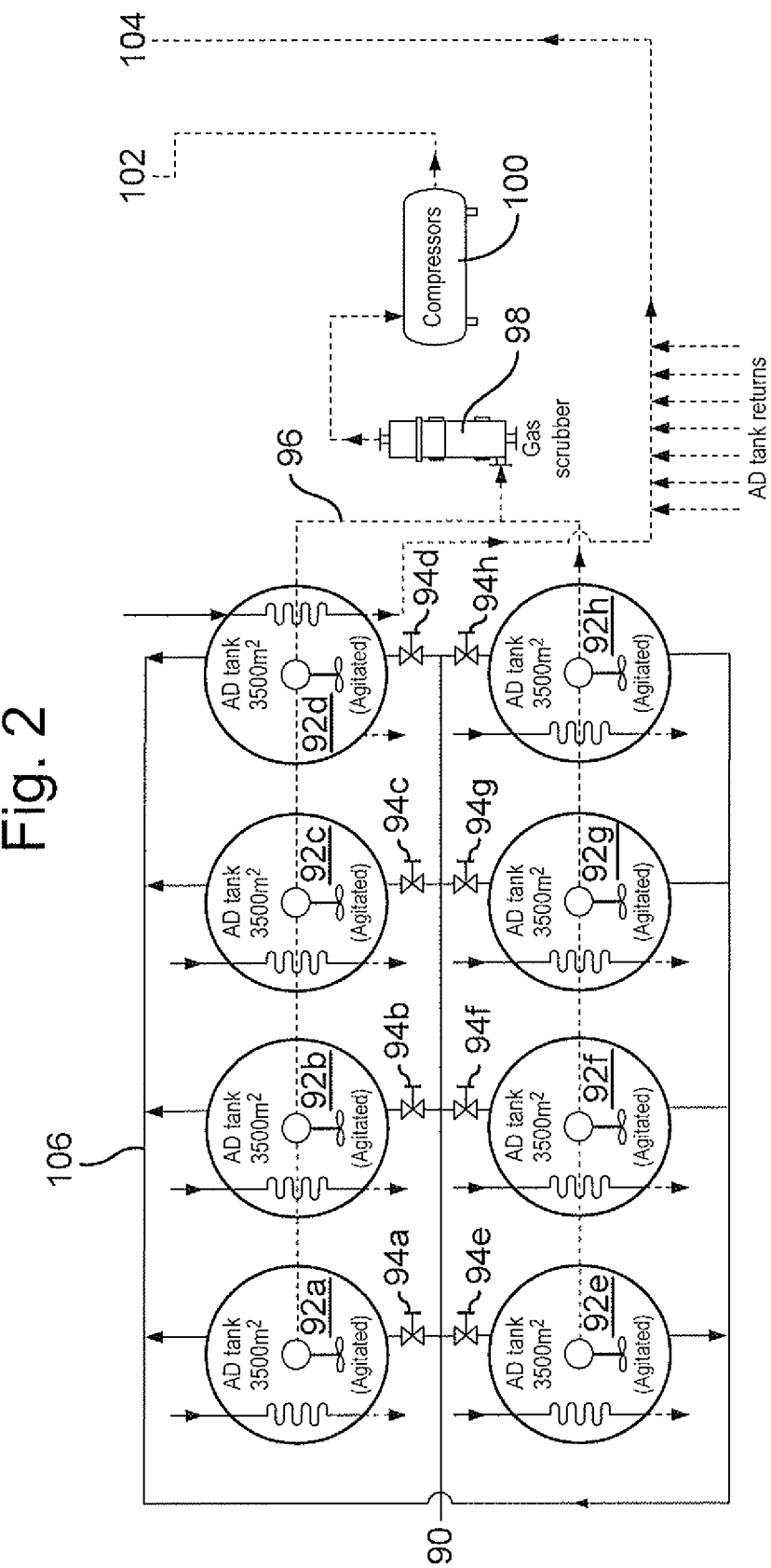
FIG. 2 shows diagrammatically an aerobic digestion plant forming a further part of the plant of FIG. 1.

FIG. 2 shows an anaerobic digestion plant forming a further part of the treatment plant of FIG. 1. It may be operated under wet conditions, solids content being <15% e.g. 2-15%, as a further example about 10%. It may also be operated under semi-dry conditions with solids content 15-20% or under dry conditions with solids content 30-40%, but these possibilities are less preferred. Line 90 leads via inlet valves 94a-94f to stirred anaerobic digestion tanks 92a-92f each holding the autoclaved organic waste component for 15-30 days e.g. about 20 days, working at a content of about 10% w/v solids content and each of liquid capacity about 2500 m$^3$, height 10 m and diameter 21 m. Gas is collected overhead and passes via common line 96 to gas scrubber 98 and then to compressor 100, compressed gas at least about 0.1 barg. e.g. about 0.25 barg. being output at line 102. Liquid heats the tanks via internal heating coils and returns at 104. Digestate from the tanks is discharged at 106. The tanks may be operated under mesophilic conditions e.g. at 35-40° C. or under thermophilic conditions. The process may be configured to use acidogenic and methanogenic bacteria together in a single stage as in the disclosed embodiment, or in a further embodiment the process may be operated in two stages, a first acidogenic stage and a second methanogenic stage.

Figure 3:
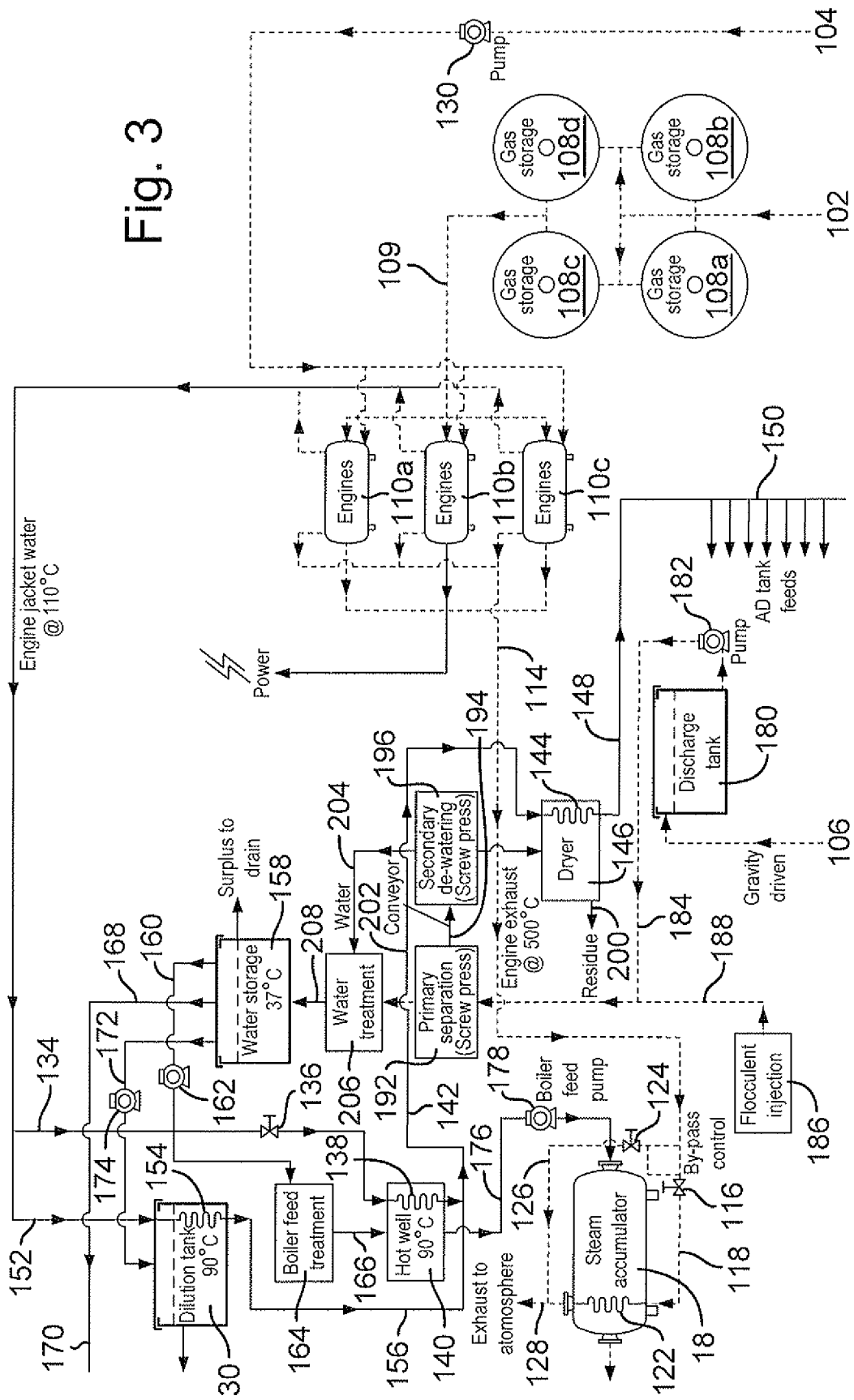
FIG. 3 shows diagrammatically gas storage plant, engines, solid treatment plant and water management and treatment plant forming part of the plant of FIG. 1.

In FIG. 3, methane-containing gas from digestion tanks 92a-92f passes via line 102 to gas storage tanks 108a-108c which can store typically some hour or hours output, 3750 m$^3$ at about 0.25 barg. Gas from the storage tanks flows via line 109 to engines 110a-110c where it is combusted to generate power. The engines may have a rated output of e.g. 1.5 MW each, discharging through their exhaust about 315 GJ of heat per day with an exhaust temperature of about 500° C. Exhaust gas from the engines passed via line 114, valve 116 and heater feed line 118 to heater coil 122 of accumulator 18, a by-pass control with by-pass 124 controlling flow of exhaust gas to by-pass line 126, the output from coil 122 and by-pass line 126 joining at vent 128. The accumulator 18 is required on demand to deliver 3.25 tonnes of steam and may be sized 13 m in length and 2.5 m diameter, giving a capacity of about 65 m$^3$.

Liquid from the digestion tanks at 104 is pumped by pump 130 as jacket water for the engines, and leaves them via line 132 at 110° C. A first branch line 134 leads through valve 136 to heater coil 138 of a hot well 140 which stores water at 90° C. Water leaving heater coil 138 passes via line 142 to heating coil 144 of dryer 146 and then at line 148 returns at 150 as warm feed to the digestion tanks 92a-92f. A second branch line 152 passes jacket water through heater coil 154 of dilution tank 30 for maintaining the contents thereof at about 90° C. and then at 156 combines with the flow in line 142.

Water storage tank 158 maintained e.g. at about 37° C. provides a feed via line 160 and pump 162 to boiler feed treatment tank 164, from which water flows to hot well 140 via line 166, the hot well providing feed via line 176 and pump 178 to steam accumulator 18. Water also flows via line 170 and a pump and an air blast cooler to cold water tank 66. A third stream from tank 158 is pumped via line 172 by pump 174 to dilution tank 30. Solids-rich discharge from the digestion tanks 92a-92f passes via line 106 to discharge tank at the same volume flow as the liquid entering the digestion tanks.

The discharge tank 180 may receive about 48 m³/hour of dilute slurry carrying about 60 tonnes per day of solids, the tank having typically a capacity of about 250 m³. Dilute slurry is pumped from the tank 180 by pump 182 via line 184 where it is combined with flocculent from flocculent injection tank 186, the combined flow passing via line 190 to a belt press or the like forming a primary separation stage 192. Water passes from the primary separation stage 192 via line 202 to treatment tank 206 and then returns via line 208 to water storage tank 158. A solids-rich stream is conveyed by conveyor 194 to a secondary de-watering stage 196 which may take the form of a screw press, solids passing via conveyor 198 to drier 146 and leaving as a solids residue stream 200. An aqueous stream from the secondary de-watering stage 196 passes at line 204 to water treatment tank 206.

The jacket water from the engines also absorbs about 315 GJ/day, the water leaving the engines at about 110° C. and being cooled during processing to about 50° C., the water flow being about 1260 tonnes/day. Heating the feedwater for the autoclaves in dilution tank 30 and heating the feedwater in the hot well 140 that feeds steam accumulator 18, in both instances from about 35° C. to about 90° C. is estimated to consume about 50 GJ/day. Maintaining the digestion tanks at 37° C. could require up to 20 Gj/day depending on ambient temperature. Removal of 45 tonnes/day of moisture from the discharge in line 106 assuming a process efficiency of 50% could require a heat input of about 225 GJ/day. Heat rejection from the hot water system can therefore be approximately balanced.

In the first and second stages of de-watering 192, 196 about 45 tonnes/cycle of water is separated, giving about 900 tonnes per day of water at 37° C. via lines 202, 204 available for re-use. Of that flow, 150 tonnes/day passes via line 172 to tank 30 as dilution water re-heated as previously stated to 90° C., the tank 30 typically being of capacity about 50 m³. About 685 tonnes per day passes via line 168, 170 for cooling and sorting and is cooled to near ambient temperatures by the air blast cooler prior to entry into the tank 66, cooling from about 37° C. to about 25° C. rejecting about 34 GJ/day of heat and the tank 66 typically being of capacity about 50 m³. About 65 tonnes per day of water passes via line 160 to tank 164 where it is upgraded to boiler feed water and supplied to steam accumulator 18. The residue 198 from the second stage 196 may have a solids content of 50%, so that some 52.5 tonnes per day are desirably removed by thermal drying at 146 using engine jacket water to remove a further 45 tonnes per day of moisture. The residue 200 may typically be 75 tonnes per day with a 20% moisture content and amounting to less than 25% of the quantity of the original waste. It is nitrogen-rich and may be added to green waste to form compost. Alternatively it may be further watered to a solids content of about 80%, mixed with low grade chopped plastics and gasified.

Experimental Trials

Figure 13:
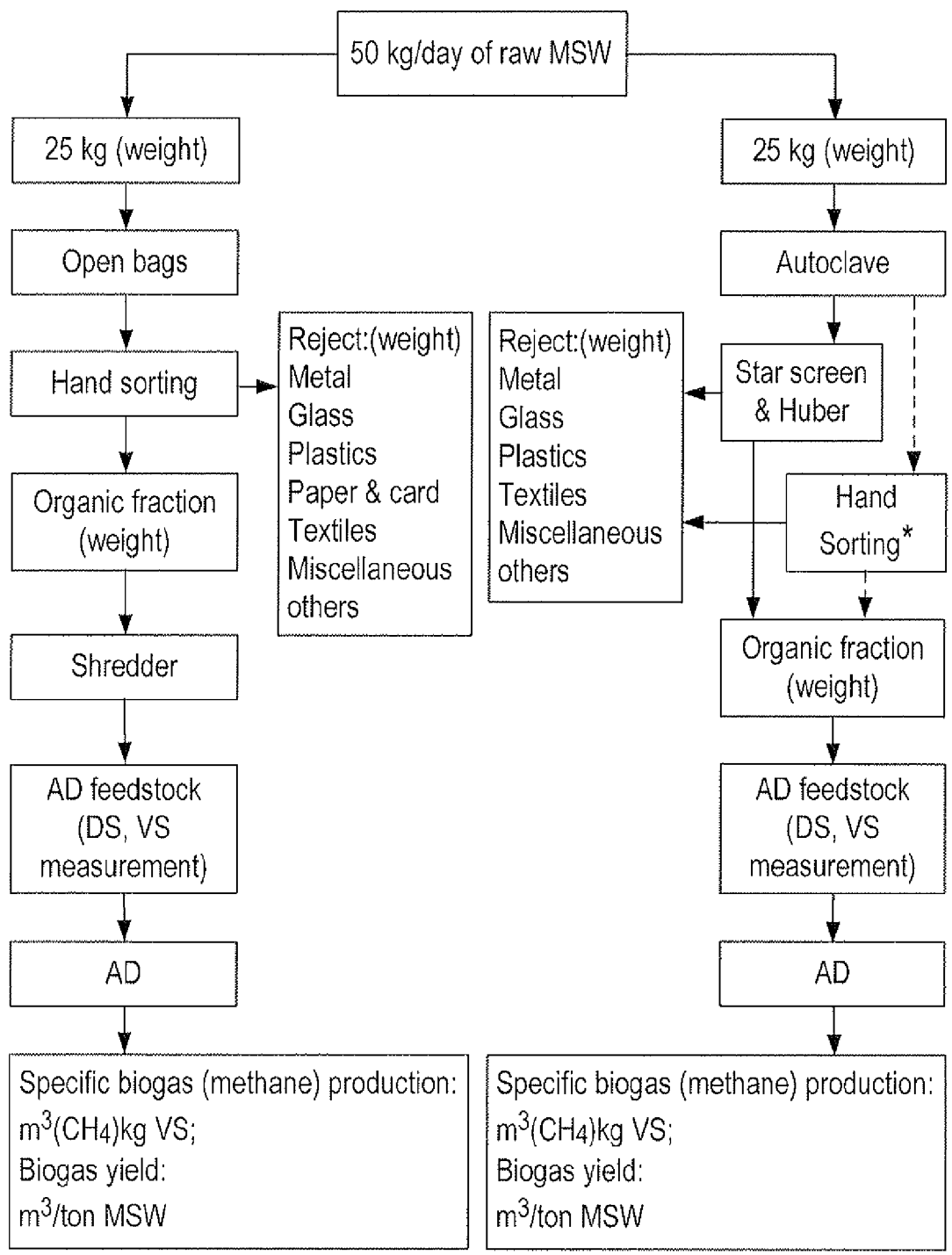
FIGS. 13 and 14 are flow charts showing procedures using the pilot scale autoclave of FIGS. 4-7 and pilot scale anaerobic digestion.

A preliminary series of experiments was carried out on a pilot scale using a single pilot-scale autoclave as shown in FIGS. 4-7 and pilot-scale anaerobic digestion. It demonstrated and quantified improvements that could be achieved using the above described autoclave to pre-treat MSW before sending it to anaerobic digestion (AD). These experiments were conducted using samples provided by a MSW collection company of raw organic waste and of a mechanically pre-treated organic fraction thereof. The results showed that:

Although gas generation was significantly affected by the nature of the waste samples provided, autoclaving the sample raw MSW gave a gas yield well in excess of a target of 65 m³/tonne of waste (FIG. 13).

The improvements obtained with the collected waste (up to a factor of 7) were due to a combination of effects. The fraction of the waste that could be digested was increased, the gas yield from each kilogram of waste sent to the digesters was also increased and the amount of material requiring disposal was reduced.

Figure 14:
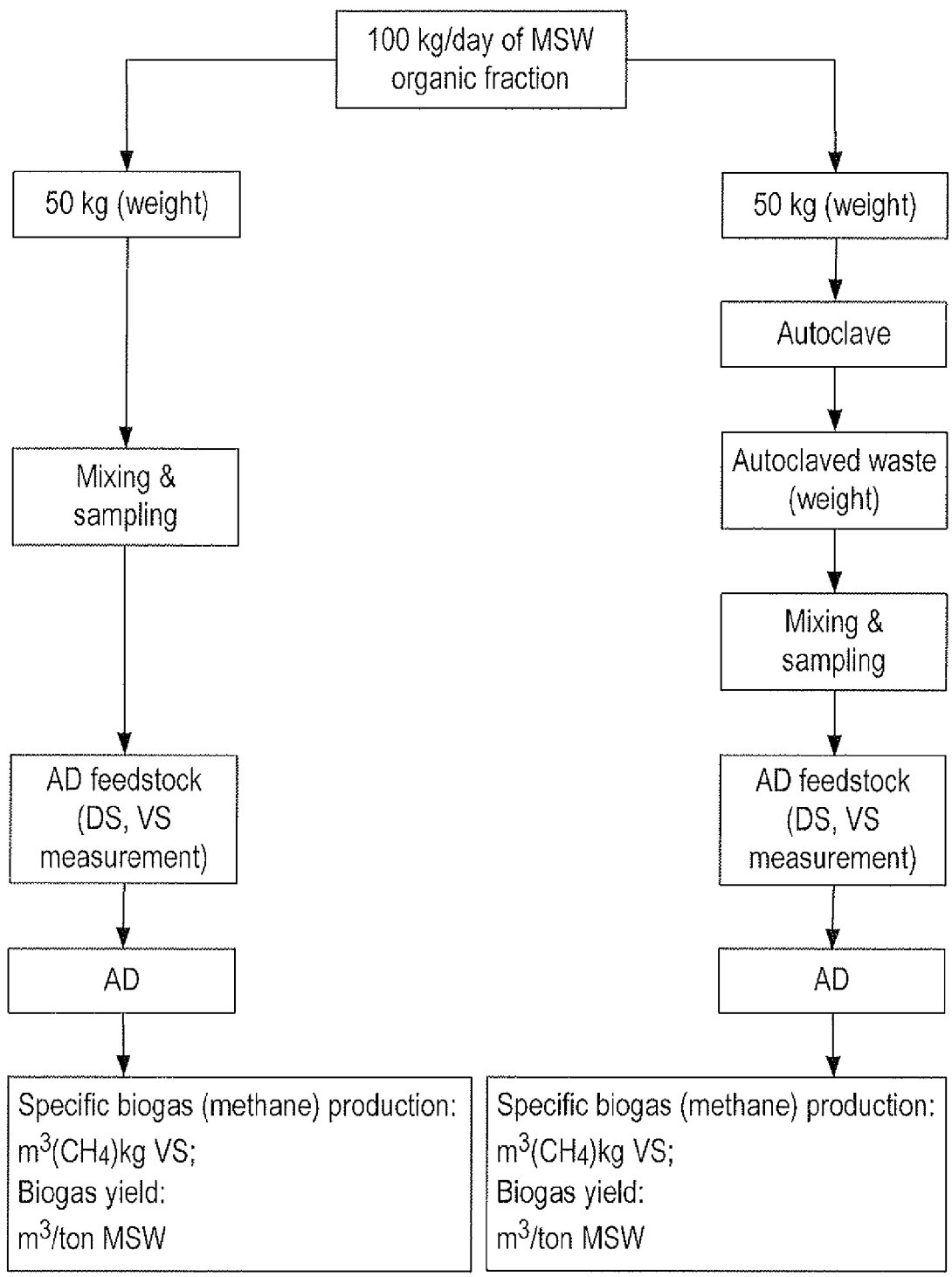

Autoclaving a second sample which was a mechanically pre-processd organic fraction of the first MSW sample gave a substantial improvement in gas yield, achieving a figure in excess of 100 m³/tonne of waste processed (FIG. 14).

Autoclaved materials were less susceptible to the development of high volatile fatty acid (VFA) concentrations than un-autoclaved material.

Steam consumption was in close agreement with predictions.

For sampling, the material was spread onto a mixing tray and mixed thoroughly, after which it was divided into four portions. 15% of each portion was then taken and remixed and re-divided into four parts. This process was repeated until a final sample of 1000 g remained, which was divided to produce samples for moisture content, volatile solids (VS) content and processing in the digesters.

For chemical analysis, pH was measured using an Accumet AB 15 pH meter. Ammoniacal nitrogen was measured using a CIL 3000 series scanning spectrophotometer. Samples were reacted with salicylate and dichloroisocyauric acid to produce a blue compound having an absorption peak at 655 nm. Volatile fatty acids were analysed using a Shimadzu GC-2010 gas chromatograph. The samples were first pre-treated by adding concentrated formic acid to make 10% formic acid solutions and then centrifuged. The supernatant liquor was analysed. Samples were compared against standard solutions (500 mg $1^{-1}$) of acetic, propionic, isobutyric, butyric, isovaleric, valeric, hexanoic, and heptanoic acids. Dried solids (DS) and volatile solids (VS) were measured gravimetrically using a fan assisted oven (105° C.) and muffle furnace (550° C.) according to standard methods. From this measurement the moisture content and ash concentration of the sample was also obtained. For analysis of evolved gas, methane and carbon dioxide was determined using a Varian CP-3800 gas chromatograph.

Figure 11:
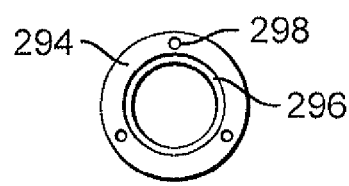

Immediately after delivery to the raw MSW and mechanically pre-treated MSW was put into refrigerated storage until it was needed for tests. Then, as shown in FIGS. 11 and 12, the two waste samples were each divided into four portions. One portion of each waste was processed each day, four days per week. Half of each was processed via the autoclave route and the other half is processed via a non-autoclave route. Mass balances across all of the units were obtained from the trial.

The handling, sorting and sampling procedures for the raw MSW involved the following stages. For the non-autoclave route (FIG. 13) the waste to be processed was weighed, the bag in which it was contained was opened and the waste was transferred onto a sorting bench and separated into fractions for metals, glass, plastics, paper and card, textiles, miscellaneous combustibles miscellaneous combustibles, putrescible and other, each of which was weighed. The putrescibles were shredded, the shredded material was placed on a mixing tray and manually mixed and then sampled. DS and VS values for each sample were measured, and the organic samples were fed into digesters. For the autoclave route, the waste was weighed, loaded into an autoclave with added water if necessary in which case the weight of the added water was noted. The cold water level in the condenser was noted, and autoclaving was carried out as indicated below. The load discharged from the autoclave was weighed, the condenser level was re-measured, and the waste was transferred onto a sorting bench for sorting into metals, glass, plastics, textiles, miscellaneous non-combustibles and others. Organic slurry from hand sorting was spread onto a mixing tray, mixed and samples were taken for anaerobic digestion.

For the mechanically pre-treated material (FIG. 14) in non-autoclave treatment the waste was weighed, spread onto a mixing tray and sampled, the DS and VS of a collected sample were measured and further samples were loaded into digesters. For the autoclave route the waste to be processed was weighed, loaded into the autoclave with added water if necessary in which case the weight of the added water was noted. The level of cold water in the condenser was recorded, the autoclave was operated as described below, the waste was discharged and weighed, the water level in the condenser was re-measured, the waste was spread onto a mixing tray and mixed. Samples of the mixed waste were taken for DS and VS measurement and for anaerobic digestion.

For autoclave treatment the load is introduced into the autoclave through its upper door, after which the autoclave is evacuated using a vacuum pump to remove incondensable gases which are adsorbed using an activated carbon filter. The autoclave is then brought up to pressure and temperature (6.2 bars abs/160° C.) by the injection of steam. When the temperatures at the lower and upper ends of the autoclave have equalised the load is left to "cook" for an appropriate period while the autoclave continues to rotate. At the end of this period the autoclave is disconnected from the steam supply and is connected to its dedicated spray condenser system which allows the autoclave to be depressurised to below atmospheric pressure. Finally a vent valve is opened to re-admit air into the autoclave and return it to atmospheric pressure. The bottom autoclave door is then opened and the load is discharged.

For digestion, twelve cylindrical constantly stirred tank anaerobic digesters (CSTR), each of which had a working volume of 1.8 liters were used. Each reactor was of PVC with a flanged gas-tight top with ports to allow feed additions, effluent removal, gas collection, and a motor-driven stirrer. The stirrers were of a picket fence design with the drive shaft inserted into the reactor through a sealed coupling; each was driven by a 40 rpm DC motor. The digesters are maintained in a water bath temperature controlled at a constant level of 37° C. Biogas was collected via a gas outlet tube connected to a 5 liter gas collector by a method of water displacement. Digestion was carried out in triplicate for each tested waste. To start the process 1.8 liter of seed inoculum was first added into each digester. When the digesters reached its designated temperature a daily feeding semi-continuous operating regime was started according to designed organic loading rates. The biogas production was monitored daily and the gas composition was being measured weekly. The pH of digestates was monitored daily and other properties such as DS, VS, ammonia and VFAs were analysed weekly.

For the raw MSW organic fraction sorted from the un-autoclaved material had a volatile solids content (VS) varying between 0.04 and 0.19 kg VS/kg raw waste for most of the period but this figure rose sharply to 0.6 kg VS/kg raw waste at the end of the period when the sample supplied was, predominantly food waste. This variation in feedstock gave rise to corresponding variation in digester performance. The corresponding figures for the autoclaved stream give a VS fraction varying between 0.18 and 0.41 kg VS/kg raw waste. The un-autoclaved waste gave gas yields in the range of 15-45 $m^3$/tonne waste, whereas the autoclaved waste gave an average gas yield of 83 $m^3$/tonne waste. This was well above the target of 65 $m^3$/tonne of waste and showed clearly that autoclaving gives a substantial improvement in the gas output from AD, driven by a near doubling in the amount of VS that can be handled in the AD plant and a near doubling of the gas yield per kg of VS. The methane concentration was about 55%, although in subsequent experiments values above 60% were achieved.

In subsequent treatment of normal black bag waste the VS from the autoclaved waste was almost 7 times higher than that from the non-autoclaved waste, resulting in about 7 times more biogas produced per tonne of incoming raw waste. The gap in specific biogas production ($m^3$/kg VS added) between both cases was not large because the autoclave process had converted most of the cellulosic materials such as paper, card, and other fabric materials into AD feedstock. Approximately 150 $m^3$ of gas from each tonne of autoclaved waste has been obtained which is well ahead of the target of 65 $m^3$/tonne.

Figure 15:
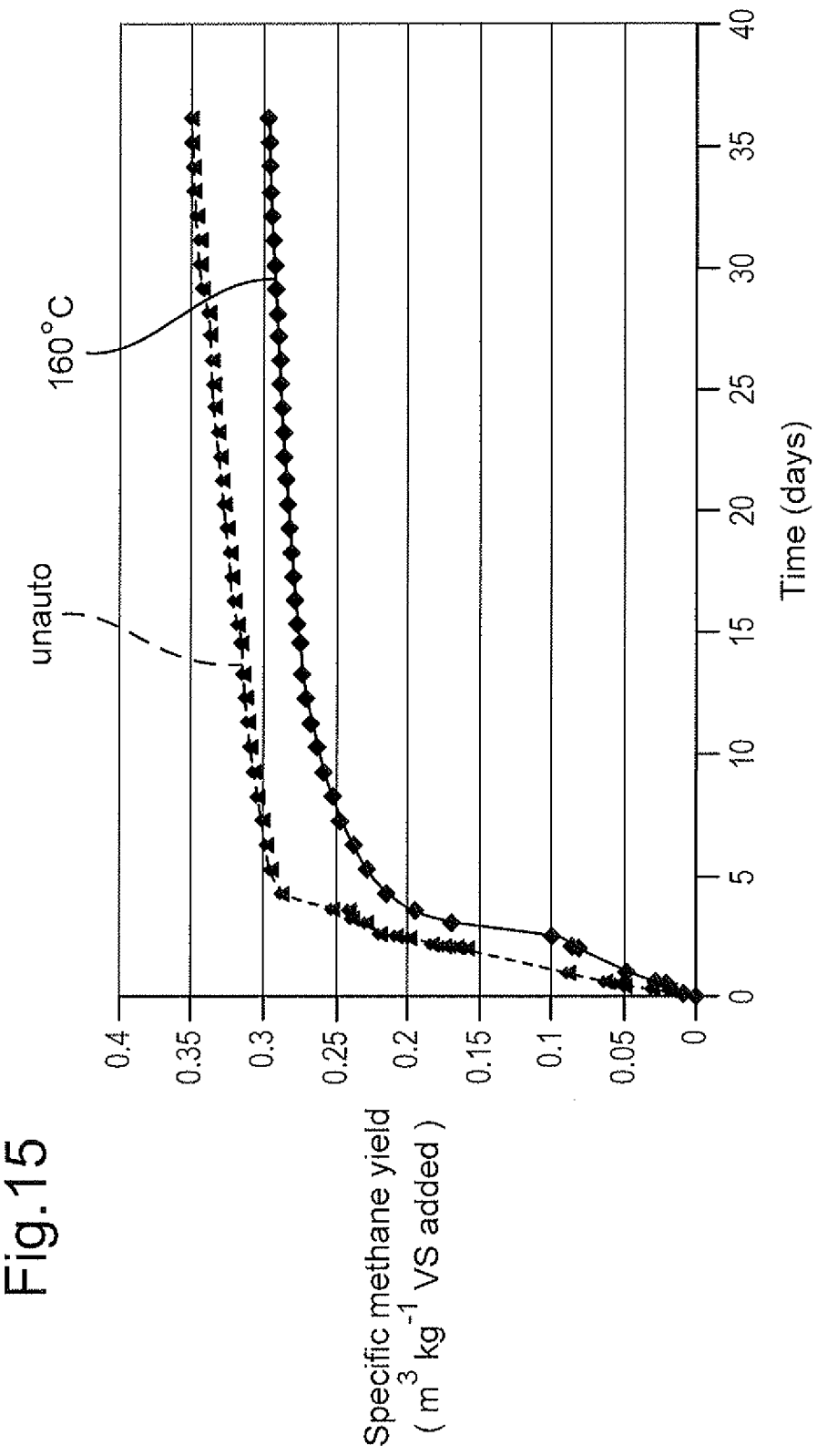
FIG. 15 is a graph of methane yield against time for anaerobic digestion of material from untreated waste and material that has been steam autoclave treated to hydrolyse at least a significant part of the cellulosic material present.

FIG. 15 presents experiment results of an anaerobic biomethane potential test on municipal solid wastes with and without autoclave (160° C. for 45 minutes) treatment. It can be clearly seen that to achieve a specific methane yield of 0.3 $m^3$/kg VS added requires a residence time of longer than 35 days for the un-autoclaved waste, whereas it takes less than 10 days to achieve the same yield when treating the autoclaved waste. If, for example, 100 tonnes per day of autoclaved and un-autoclaved waste streams are treated (solids concentrations adjusted to 10% for both cases). Then the volume of AD tank required for both cases can be calculated as follows:

Un-autoclaved waste–digester Volume=100×35=3500 $m^3$
Autoclaved waste–digester Volume=100×10=1000 $m^3$ It is apparent that autoclave pre-treatment under conditions that involve significant hydrolysis of the cellulosic material present has the potential to reduce the size of the AD tanks required by 70%. The benefits are further apparent by reference to the accompanying tables:

TABLE 1

MSW hand sorting result (three months average):

| Category | Concentration, % | |
|---|---|---|
| | Un-autoclaved waste | Autoclaved waste |
| Organic fraction | 23.9 | 82.7 |
| Metal | 6.0 | 3.5 |
| Glass | 3.7 | 1.0 |
| Plastics | 19.6 | 7.1 |
| Paper and cardboard | 29.3 | N/A |
| Textiles | 6.6 | 3.4 |
| Miscellaneous combustibles | 7.5 | 1.6 |
| Miscellaneous non-combustibles | 1.2 | 0.5 |
| Other | 2.2 | 0.2 |
| Total | 100 | 100 |

TABLE 2

Solids analysis results of organic fractions of the MSW (three months average):

| Category | Analysis results | |
|---|---|---|
| | Un-autoclaved waste | Autoclaved waste |
| Dry solids (DS), % | 42.2 | 18.3 |
| Volatile solids (VS), % | 32.4 | 14.8 |
| VS available for AD derived from raw waste, kg VS/ton of MSW | 87.1 | 290.6 |

The above tables illustrate the sorting and solids analysis results of a three month trial on MSW. It can be seen that the autoclave treatment could produce 3.3 times more VS for anaerobic biomethane conversion. And ultimately up to 8 times more biogas could be generated from autoclaving and AD of one ton of MSW than AD of untreated one ton of MSW (see Table 3).

TABLE 3

Summary result of AD of autoclaved and non-autoclaved MSW

| Parameter | autoclaved | non-autoclaved | autoclaved | non-autoclaved | autoclaved | non-autoclaved |
|---|---|---|---|---|---|---|
| HRT, days | 40 | 40 | 27 | 27 | 20 | 20 |
| Loading rate, kgVS/m$^3$/day | 2 | 2 | 3 | 3 | 4 | 4 |
| pH | 7.20 ± 0.04 | 7.16 ± 0.03 | 7.08 ± 0.04 | 7.09 ± 0.05 | 7.14 ± 0.03 | 7.11 ± 0.04 |
| NH$_3$—NH$_4$, mg/l | 906 ± 40 | 980 ± 77 | 547 ± 53 | 983 ± 55 | 485 ± 37 | 752 ± 102 |
| VFA, mg/l | 55 ± 6 | 59 ± 8 | 77 ± 2 | 87 ± 4 | 275 ± 20 | 309 ± 18 |
| TS content, % | 3.5 ± 0.2 | 3.9 ± 0.5 | 4.0 ± 0.3 | 4.2 ± 0.3 | 4.3 ± 0.2 | 4.7 ± 0.1 |
| VS content, % | 1.9 ± 0.1 | 2.1 ± 0.2 | 2.5 ± 0.2 | 2.7 ± 0.3 | 2.7 ± 0.1 | 3.3 ± 0.3 |
| Specific biogas production, m$^3$/kg VS added | 0.53 ± 0.02 | 0.47 ± 0.02 | 0.52 ± 0.04 | 0.44 ± 0.04 | 0.49 ± 0.02 | 0.37 ± 0.01 |
| Specific methane yield, m$^3$CH$_4$/kg VS added | 0.32 ± 0.01 | 0.28 ± 0.01 | 0.31 ± 0.03 | 0.26 ± 0.02 | 0.30 ± 0.01 | 0.22 ± 0.01 |
| Biogas production, m$^3$/t MSW | 148 ± 5 | 25 ± 1 | 151 ± 12 | 19 ± 2 | 147 ± 6 | 17 ± 1 |
| VS removal, % | 76.6 ± 1.1 | 73.6 ± 2.2 | 69.2 ± 2.5 | 66.5 ± 3.3 | 65.8 ± 1.7 | 58.1 ± 3.6 |

Door for Full-Scale MSW-Treatment Autoclave

FIGS. 16-26 show a door arrangement for a full-scale autoclave for treating municipal solid waste and which is intended to facilitate cleaning and minimise the problems created by foreign matter from the load becoming trapped within the door mechanism and interfering with operation of that mechanism.

Referring to FIGS. 16-20, there is provided an annular rim 310 for welding to an end of an autoclave body or tunnel, the rim being formed with a recess 312 for so that it may be fitted into and welded to the wall of the autoclave body. The outer surface of the rim 312 is formed with a flat track 314 which provides a bearing surface on which roller bearings 316 of lock ring 318 run to permit the lock ring to be rotated between locking and release positions. Immediately outward of track 314, rim 310 is formed with retaining recess 320, rim flange 321 and radially directed rim closure face 322. Rim 326 has an outwardly protruberant region at the inner end of closure face 322 defined by frustoconical alignment face 326, radially directed front face 328, axially directed inner face 330 and outwardly tapering male frustoconical face 332. Closure face 324 is formed with inner and outer annular seal recesses 334, 336 for respective seals 338, 340 and the alignment face 326 also has recesses 342 for inserted alignment pads 344 e.g. of phosphor bronze.

Lock ring 318 comprises a multiplicity of circumferentially spaced locating blocks 350 attached between inner annular plate 352 and outer annular plate 354, the inner plate 352 carrying the roller bearings 316, and jacking mechanisms (not shown) and the outer plate 354 being formed with inwardly facing circumferentially spaced castellations 356 aligned with the locating blocks 350. Each plate 352, 354 is a simple annulus if uniform thickness and therefore does not contribute to the entrapment of wet mass as an autoclave discharge door of this structure is opened. Each bearing block is generally of inwardly-facing U-shape in end view with inner legs 360 fitting into recesses 320 in which they are retained, and with outer legs 362 locating behind castellations 356. The inner legs 360 are of constant thickness for location into recess 320 and their inner faces have attached thereto e.g. by fixing screws 363 wear plates 364 e.g. of graphite and/or glass-filled PTFE, PEEK, acetal other non-hygroscopic low friction plastics material, PTFE being preferred owing to its low friction properties. The outer legs 362 are tapered in order to cam the door to its fully closed position and have wear plates 366 also of low friction material replaceably secured in position by fixing screws 368. By the use of these replaceable elements of low friction material ease of replacement is achieved and interengaging metal-on-metal elements are avoided. It will be noted that the blocks where they fit between plates 352, 354 are also of simple shape with a minimum of surfaces where wet mass can catch or accumulate. The open spaces between the blocks promote drainage and facilitate cleaning with water or air jets. Rotation of the lock ring 318 between its locking and release positions may be by pneumatic or hydraulic jacking as is conventional in the autoclave art.

Figure 16:
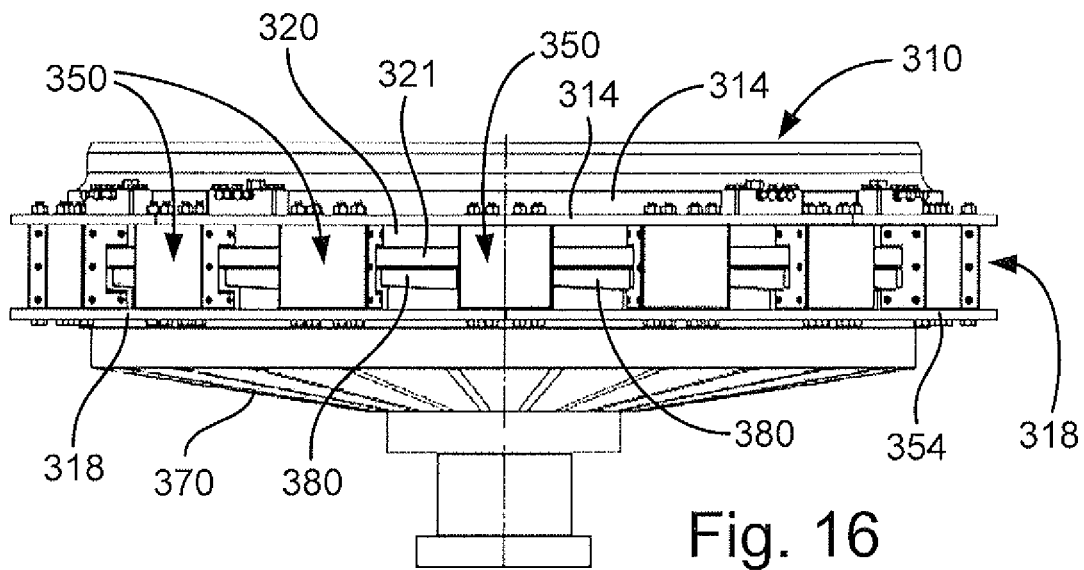
FIG. 16 is a plan view of a rim for fitting to a pressure vessel of an autoclave, a locking ring carried by the rim, and a door closed up to the rim, the locking ring being in a release position.
Figure 17:
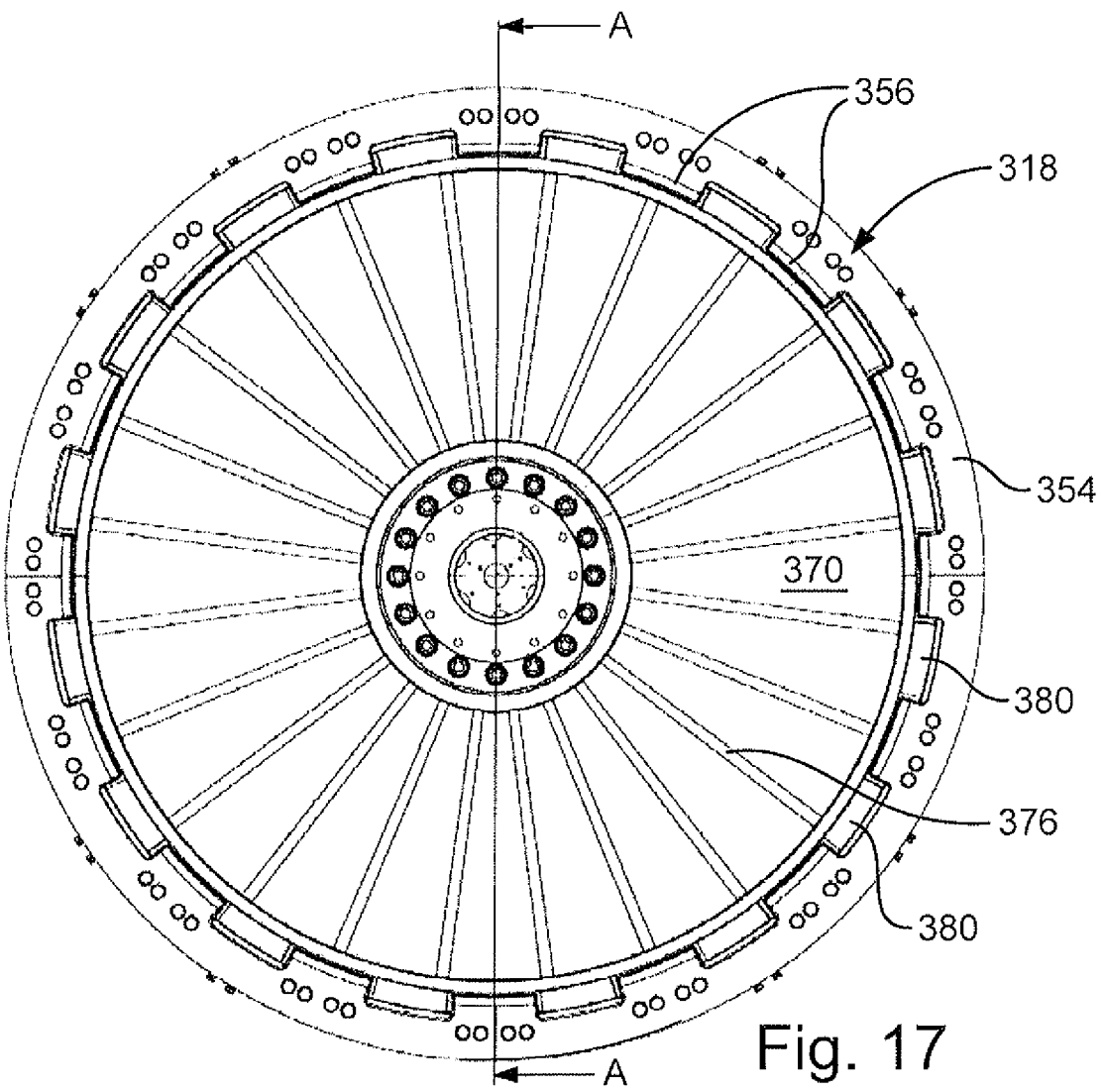
FIG. 17 is a view of the door and the locking ring in exterior elevation.
Figure 18:
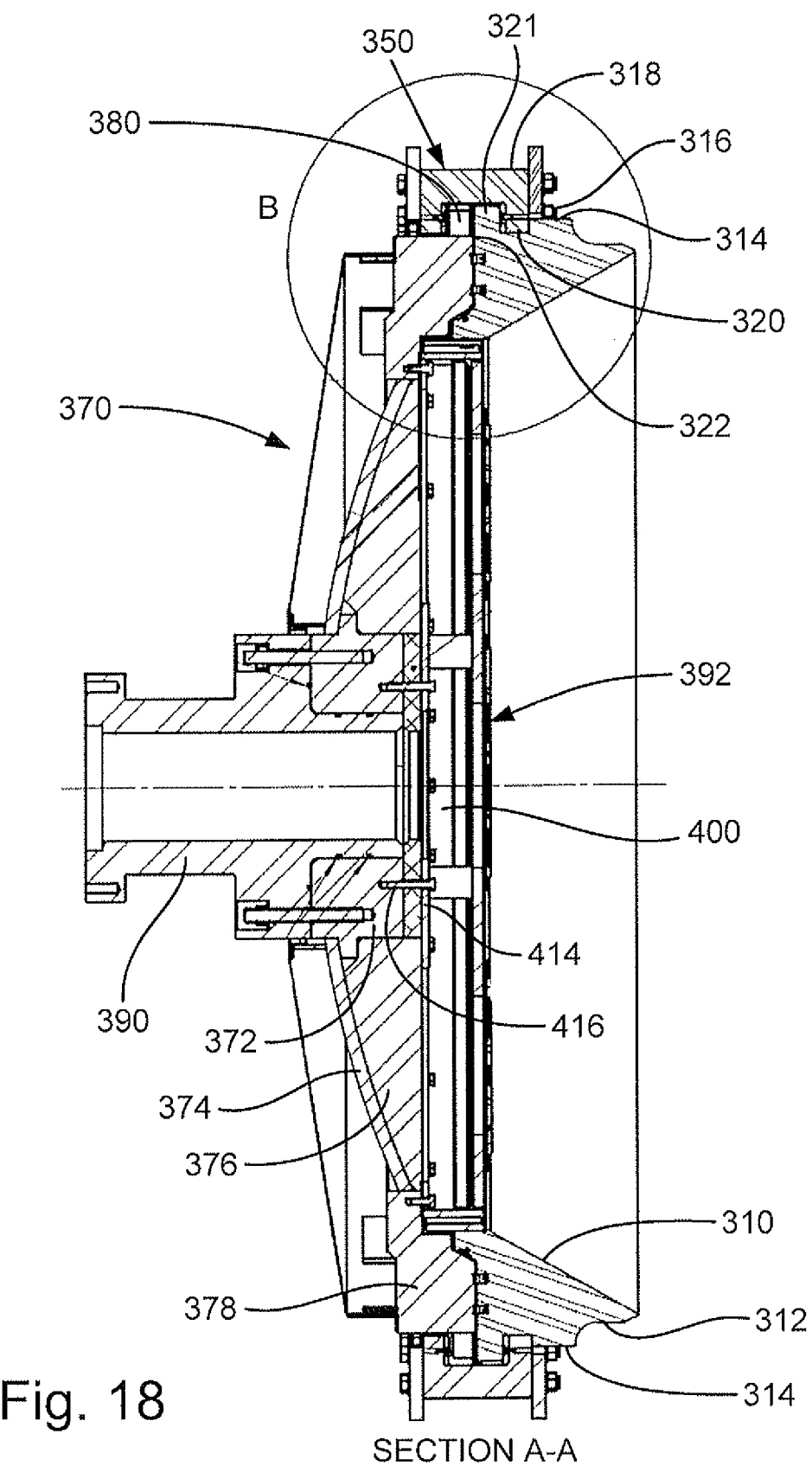
FIG. 18 is a section of the rim, locking ring and door
Figure 19:
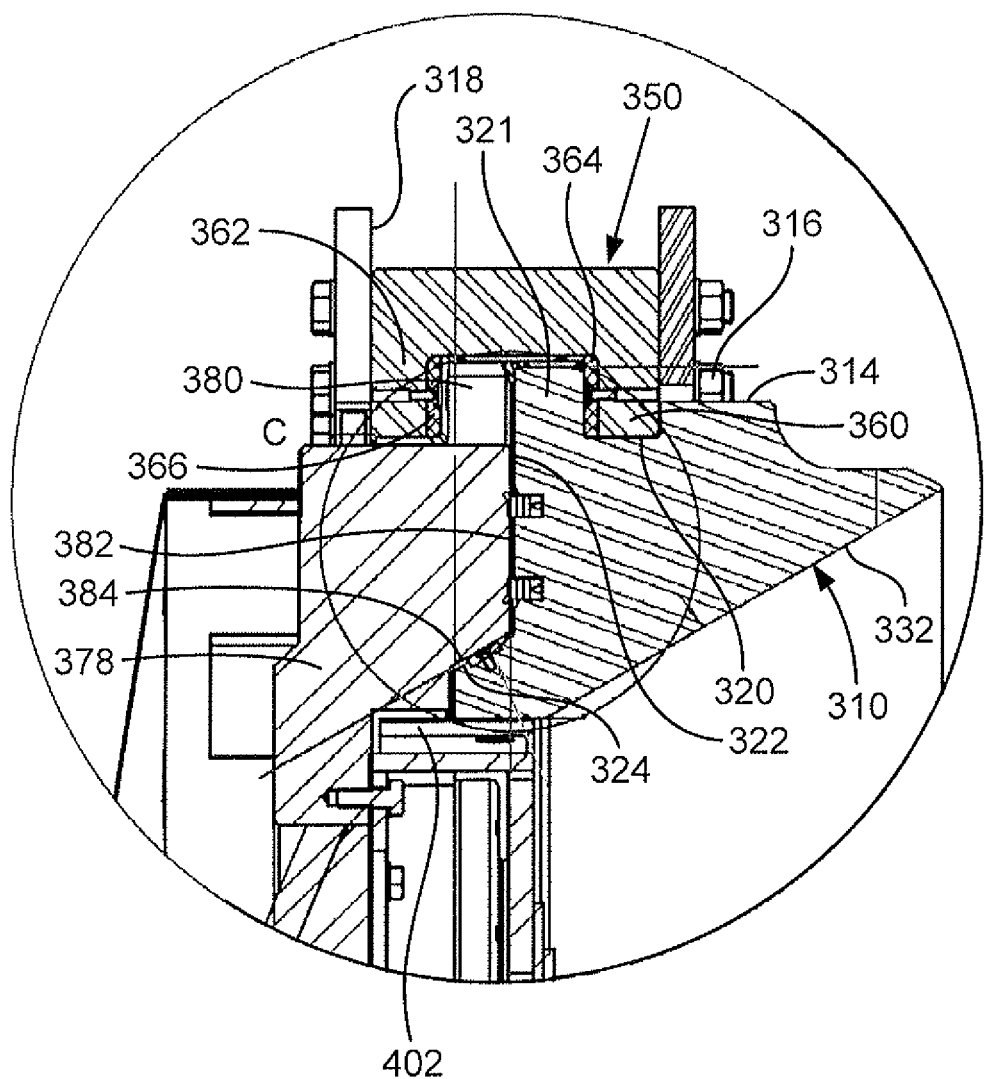
FIGS. 19 and 20 are enlarged detail views.
Figure 20:
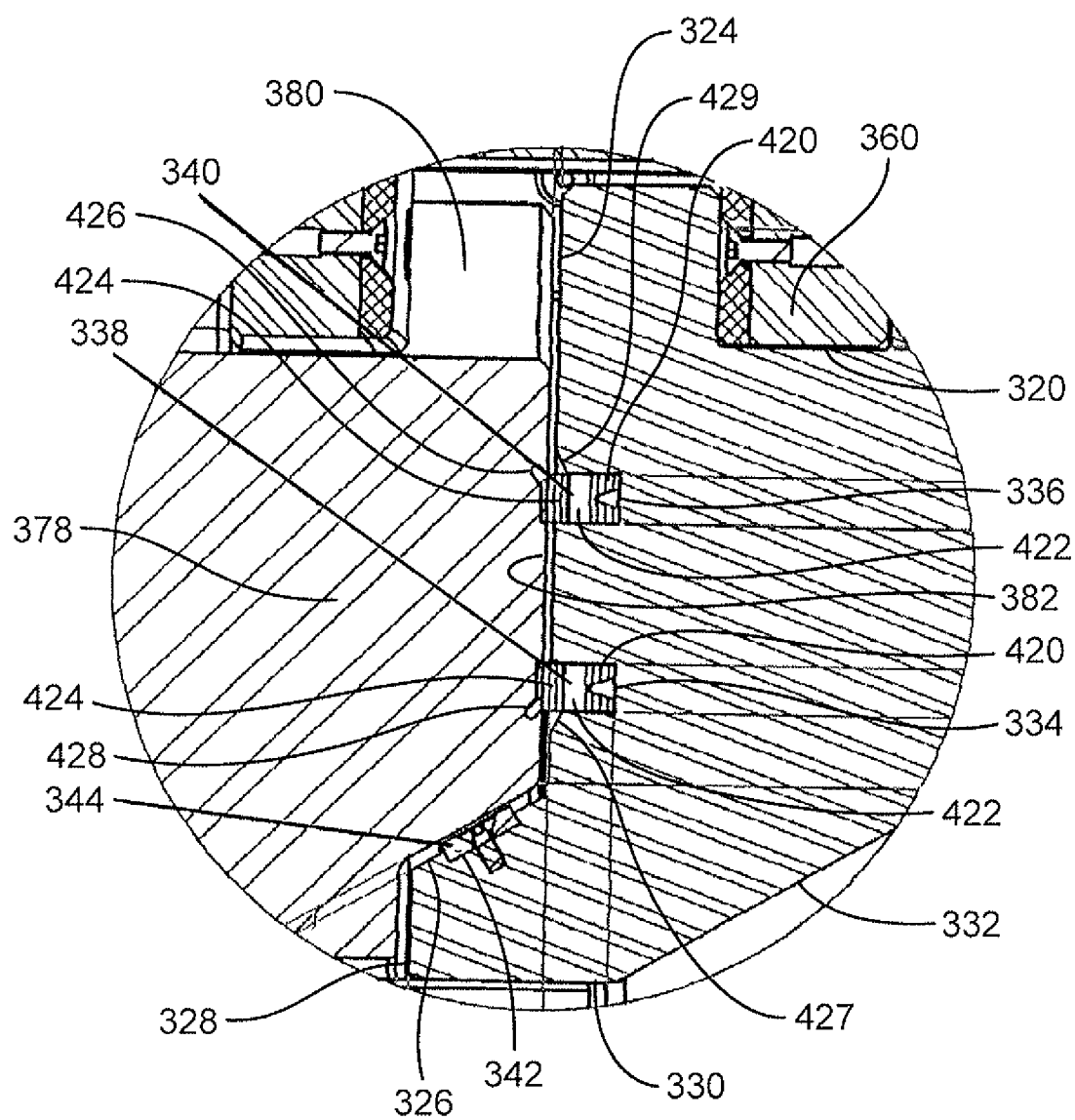
Figure 21:
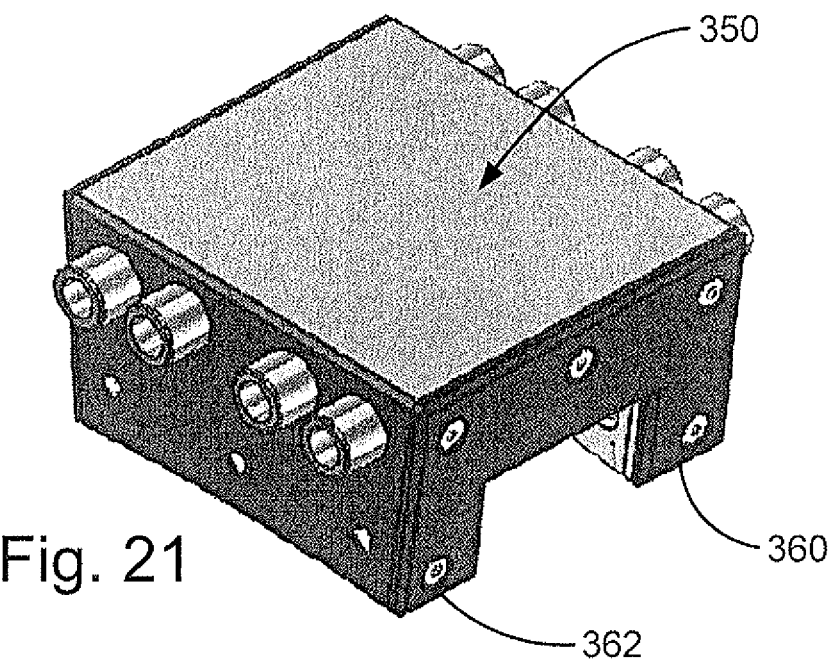
FIG. 21 is a trimetric top view of a block forming part of the locking ring of FIGS. 16-19 and FIG. 22 is a sectional view of the block.
Figure 22:
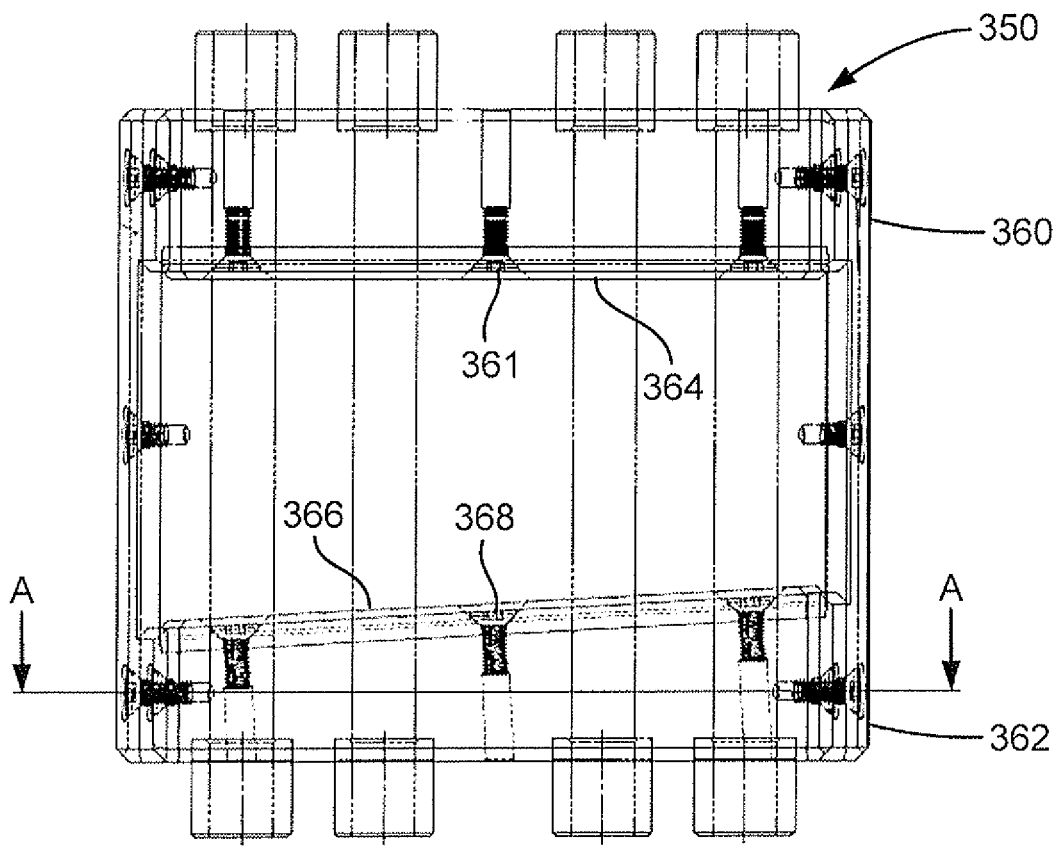
Figure 23:
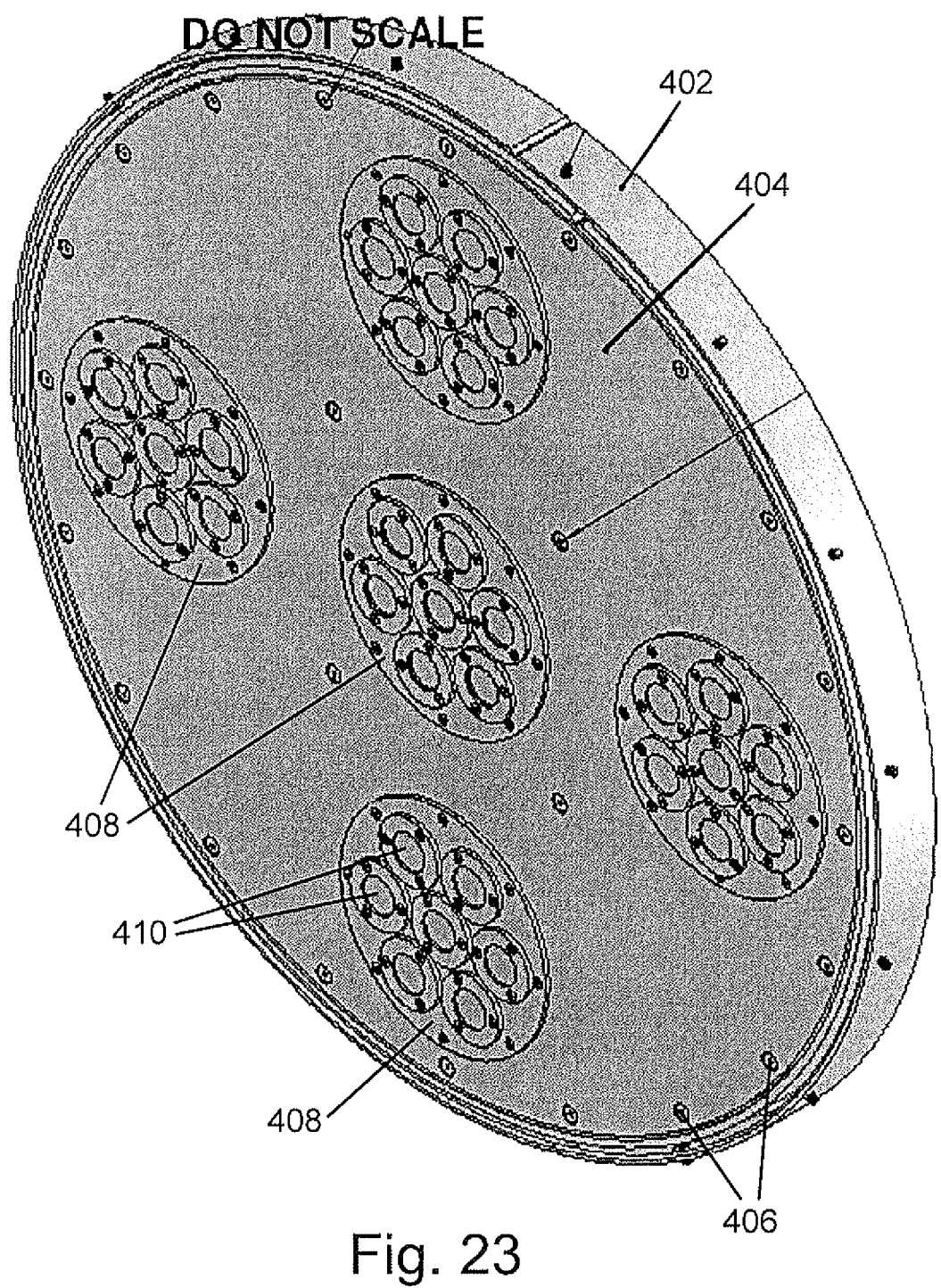
FIG. 23 is a trimetric view of part of the plenum chamber assembly that fits into the door of FIGS. 16-20 showing the face that is directed towards the autoclave body.
Figure 24:
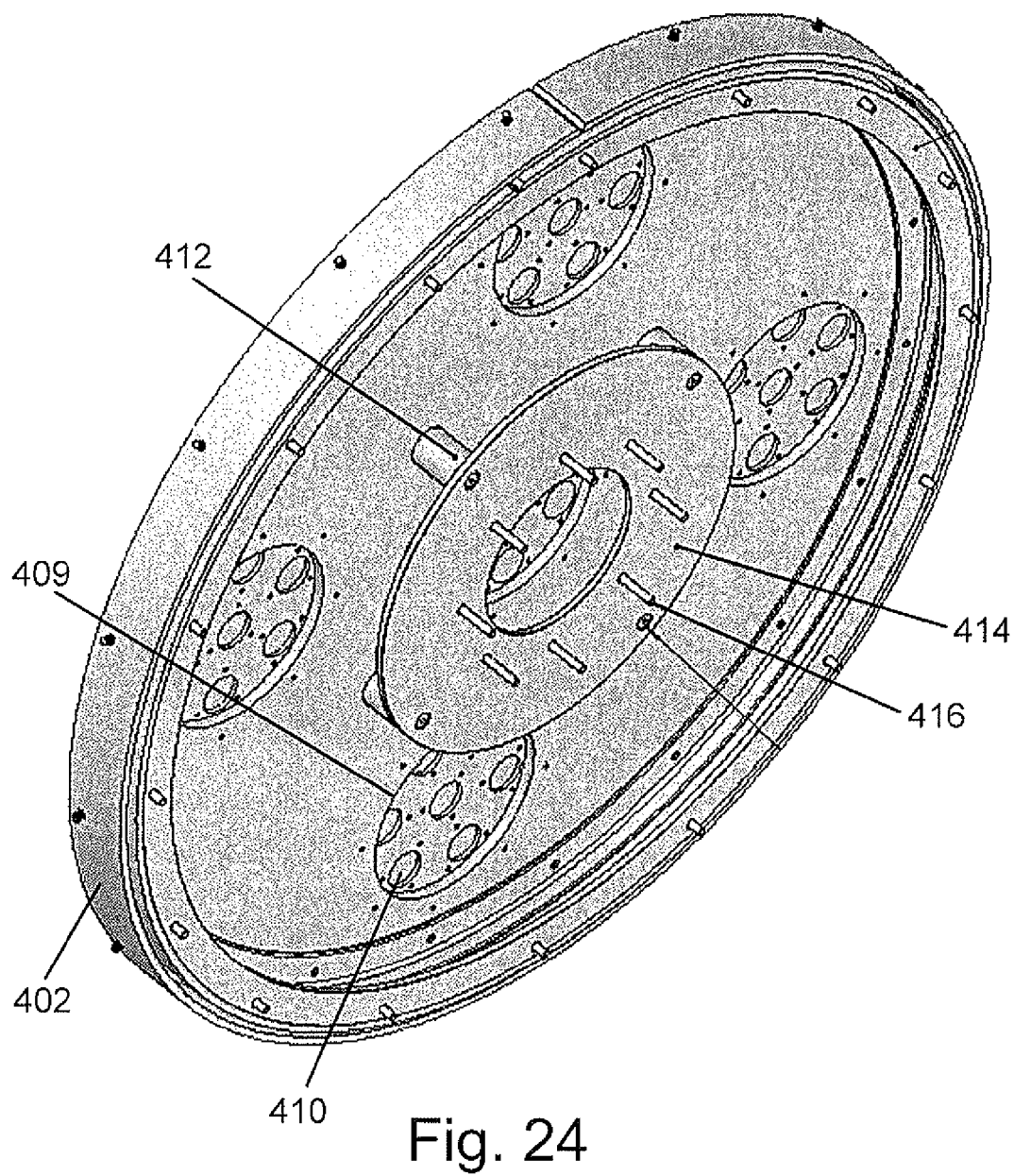
FIG. 24 is a further trimetric view of the part of the plenum chamber assembly showing the face that is directed towards the door and FIG. 25 is a section of the plenum chamber assembly.
Figure 25:
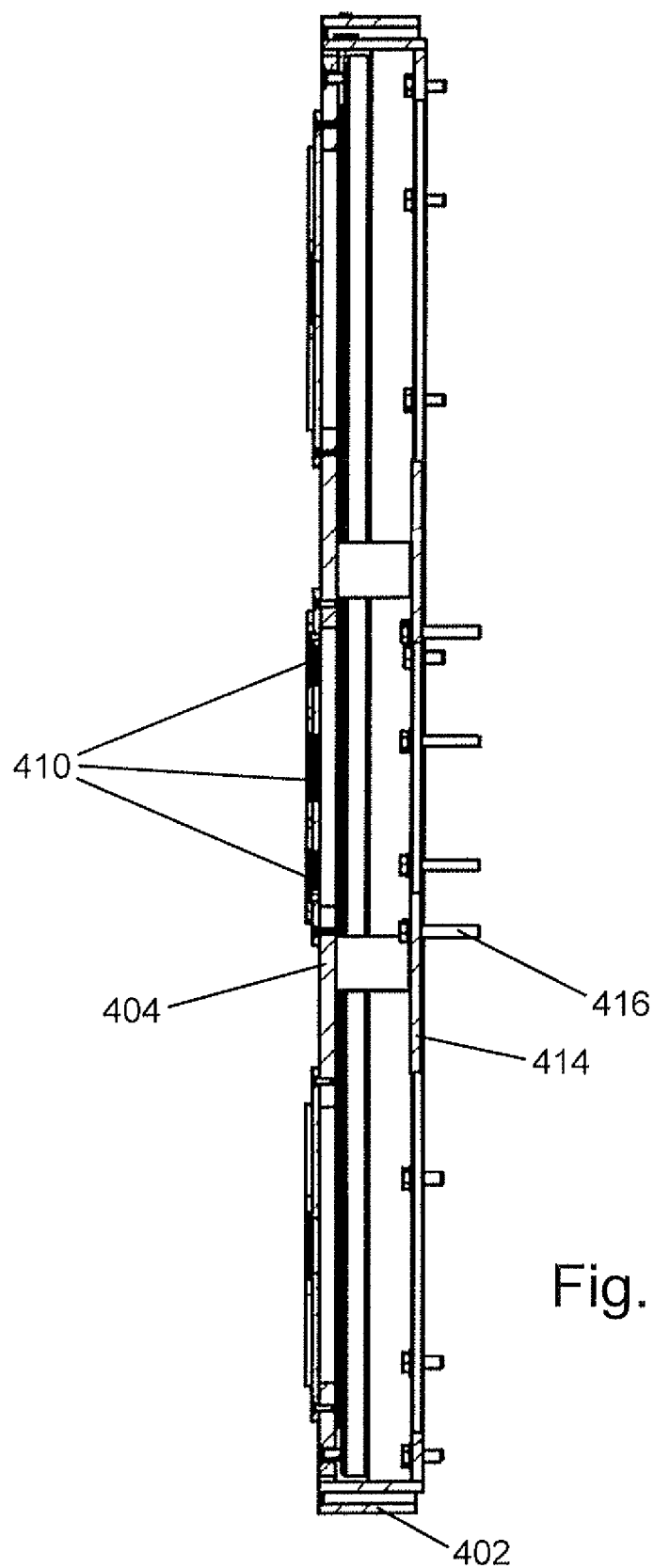

Door 370 comprises tubular hub 372, dished door plate 374 formed on its inner face with ribs 376 and terminating in flange 378 formed with circumferentially spaced castellated lugs 380 configured to fit between the blocks 350 as can be seen in FIGS. 16 and 17, in which locking ring 318 is in its release position. As seen in FIG. 16, the castellations 380 are of wedge profile matching the wedge surfaces of legs 362 with which they interlock to close the door and also to cam or wedge-lock the door into its fully closed position. Inner radially directed closure face 382 opposes closure face 322 and female frustoconical alignment face 384 opposes alignment face 326. A combined outer hub and steam supply tube 390 enables the door to be controlled for translational movement into and out of engagement with tunnel rim 310 and also provides a route for steam to a plenum assembly 392 of the door.

Figure 26:
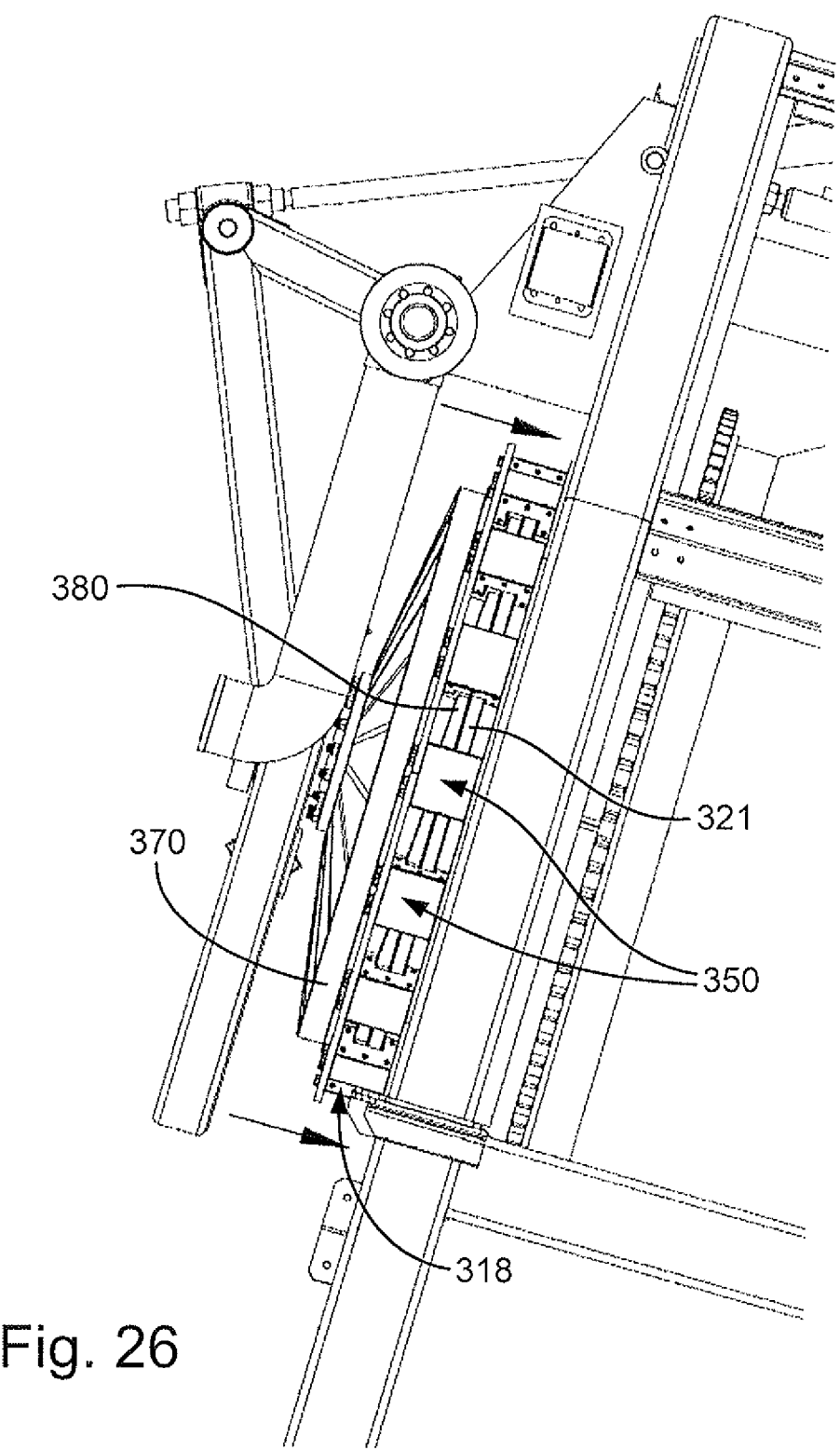
FIGS. 26-28 show portions of an end of an autoclave, a locking ring, a door and a door mechanism showing the door in fully closed, partly open and fully open positions.
Figure 27:
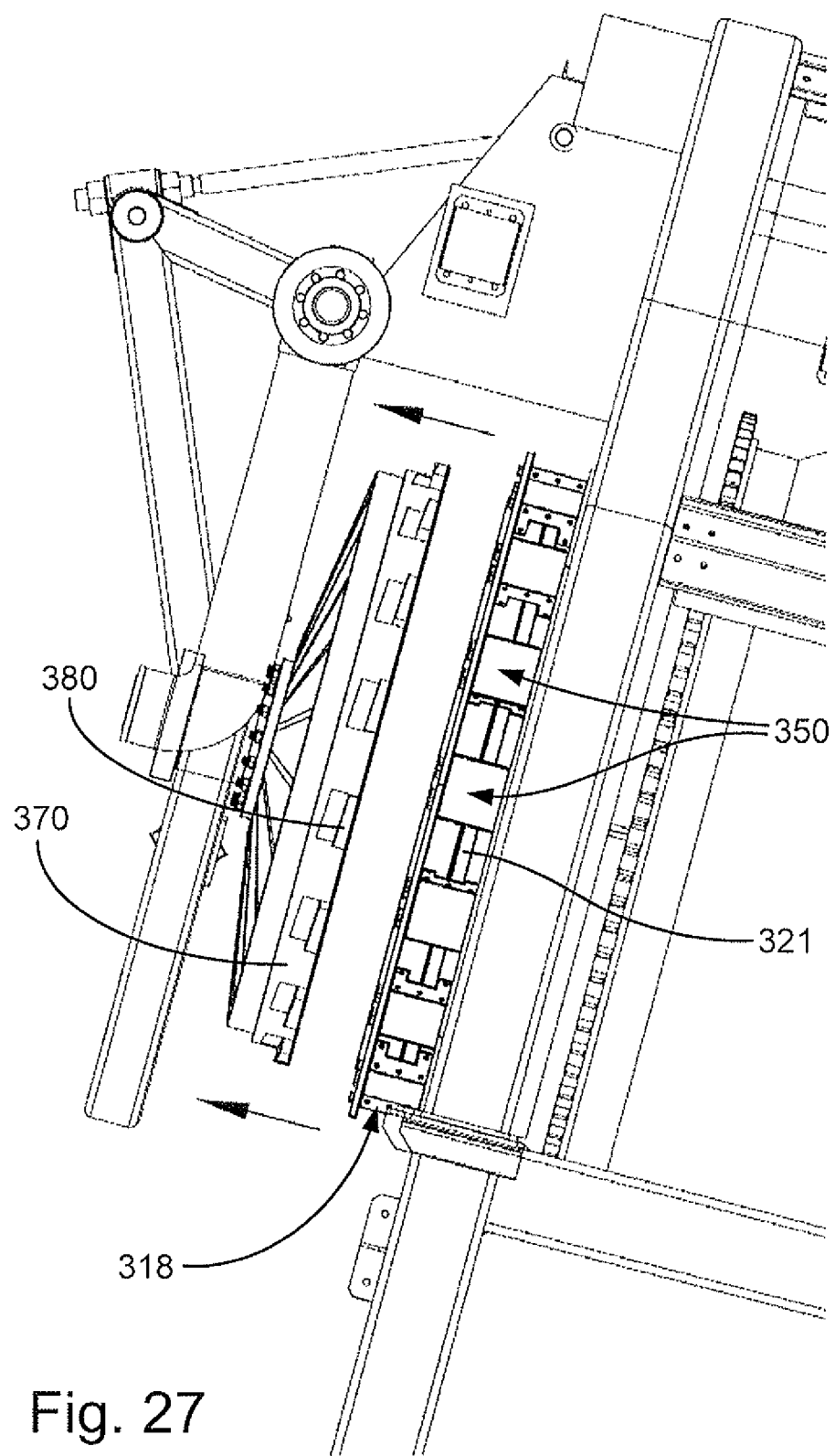
Figure 28:
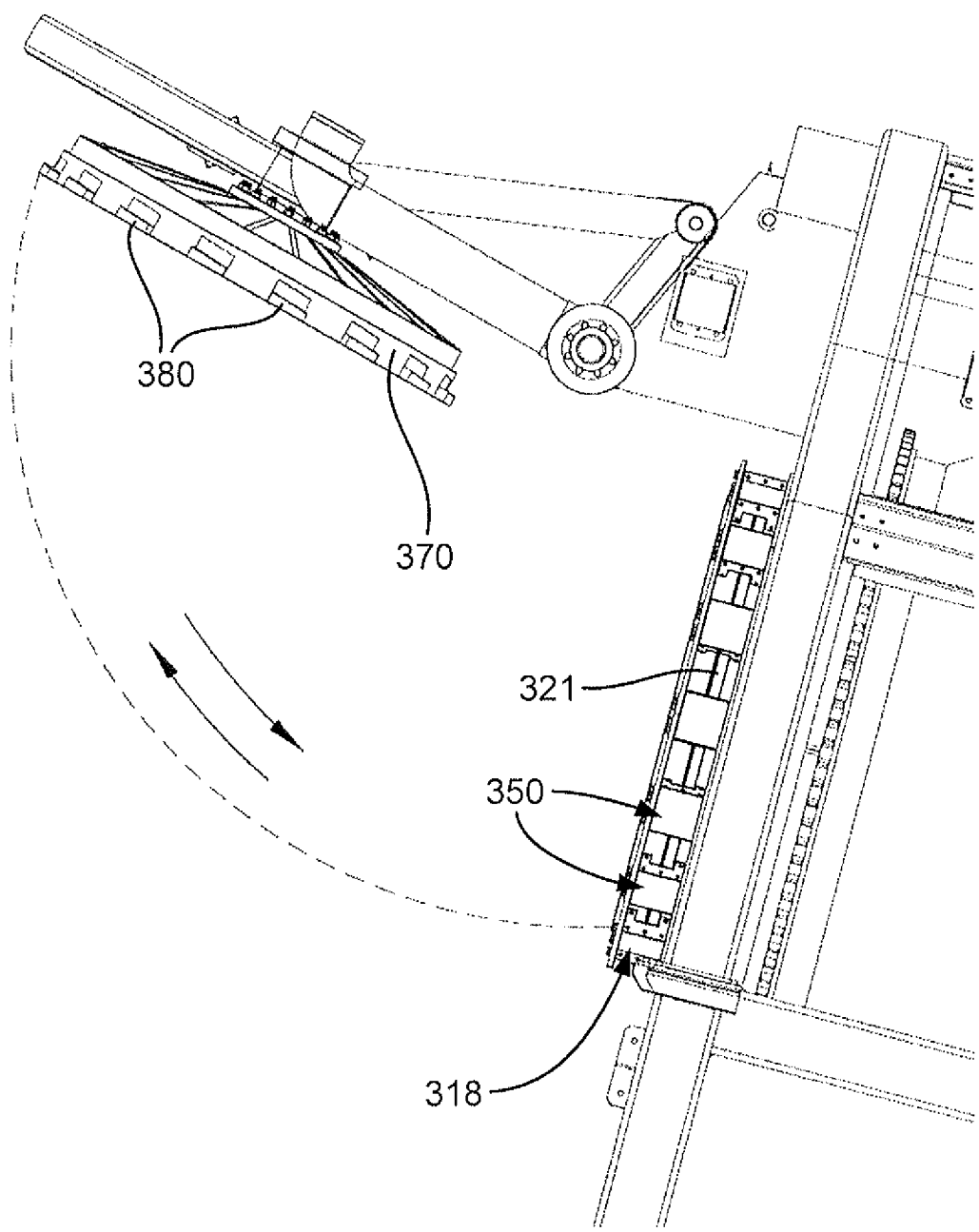

Plenum chamber 400 of the door can be fed with steam via supply tube 390. Plenum ring 402 has at one end a flange to which inner plate 404 is attached by fixing screws 406. The plate 404 carries groups 408 of sintered stainless steel disks 410 through which team flows from the plenum chamber into the tunnel or body of the autoclave. It will be noted that there are five groups 408 each containing seven discs 410 so that there are in this embodiment 34 discs 408 whose area collectively exceeds the area of the steam passage in supply tube 390 so that the discs 408 impart only relatively insignificant pressure drop to steam flowing into the autoclave. Spacing pillars 412 connect plate 404 to mounting plate 414, the mounting plate being attached to hub 372 by means of fixing screws 416. As is apparent in FIG. 19 the plenum ring 402 opposes and fits within the face 330 of the rim 310 when the door is closed. At the same time frustoconical surfaces 326 and 384 cooperate to position the door correctly and cause the door to be self-aligning as it closes. For this to be possible, the initial travel of the door to and from its fully locked position must be linear, even though the door mainly swings from and into closing engagement with the rim 310 (FIGS. 26-28). Furthermore, in the commercial-scale embodiment discussed above, the autoclave at the end of its cycle contains >15 tonnes of wet mass, and opening the lower door results in an abrupt release of that material. The initial axial travel promotes downward gushing of the wet material rather than lateral spraying of the material, and the open structure of the locking ring assists drainage Referring to FIG. 20, the inner and outer gaskets 338 and 340 are formed with inner deformable regions 420, central less deformable regions 422 and outer deformable regions 424. Each gasket is formed with a small deformable tongue 426, 428 (shown in FIG. 20 as if the door was not present) which as the door is closed becomes compressed into recesses 427, 429 which are adjacent the main gasket recesses 334, 336. The tongue 428 is on the inner side of inner gasket 338 and the tongue 426 is on the outer side of the gasket 340. Tongue 428 resists pressure within the autoclave when steam pressure is applied and tongue 426 resists atmospheric pressure when the autoclave is operated under reduced pressure or vacuum conditions. The tongues effectively provide self-energising seals insofar as that the greater the applied pressure differential the greater the sealing action, and they together avoid development of reduced pressure in the region between seals 338, 340. It is therefore possible to open the autoclave door after the autoclave has been operating under reduced pressure without damage to seals 338, 340. Provision of two tongues or flaps on a single seal would not work, and under vacuum conditions the seal would act as a suction cup making it difficult to open the door without pulling the seal out from its recess.

Various modifications may be made to the embodiments described above without departing from the invention. For example, depending on the relative importance of power and combustible fuel, instead of supplying the methane-containing gas to an internal combustion engine, part could be fed to a boiler for raising steam for supply to the autoclave and also for supplying hot water to the anaerobic digestion stage and the remainder could be upgraded to biomethane by removal of carbon dioxide in whole or in part.

The invention claimed is:

1. A rotary autoclave having an interior for treating solid waste, which is downwardly inclined towards its discharge end and which has a door at the discharge end, means in said door being provided for injecting steam through said door via a plenum chamber in said door into the interior of said rotary autoclave to treat a load of said solid waste, the plenum chamber communicating with the interior of the autoclave through at least one one-way device leading directly from the plenum chamber into the interior of the autoclave, the at least one one-way device being configured to prevent the solid waste from entering the plenum chamber from the interior of the autoclave, said plenum chamber being defined between a region of the door and a plate secured to the door at a small spacing inwardly of said door, at least one outlet being defined in the plate, and said at least one one-way device being fitted to said at least one outlet.

2. The rotary autoclave of claim 1, having one or more of the following features:
   (a) a plurality of one-way devices providing parallel paths from the plenum chamber into the interior of the rotary autoclave;
   (b) the cross-sectional area of the path or paths from the plenum chamber into the interior of the rotary autoclave defined by said at least one one-way device is equal to or greater than the area of an inlet into the plenum chamber for injected steam;
   (c) the at least one one-way device is of porous sintered metal;
   (d) the at least one one-way device is a mushroom or poppet valve;
   (e) the door carries a rotary seal for connecting a steam pipe to a steam inlet in the door for injection of steam into the autoclave as the rotary autoclave is rotated;
   (f) an inlet door for waste at its upper end, and an inlet in said door for water to be sprayed into the rotary autoclave to condense steam therein;
   (g) generally helical internal flights and a drive configured to rotate the flights during steam injection in a direction such that the generally helical internal flights lift the solid waste from the discharge end into the body of the rotary autoclave;
   (h) load sensors at upper and lower ends of said rotary autoclave for sensing load while the generally helical internal flights are lifting the waste from the lower end, equalization of the load sensed by said sensors at the upper and lower ends compared to the load sensed by said sensors at the end of waste introduction indicating that lifting is taking place;
   (i) pressure sensors at upper and lower ends of the rotary autoclave for sensing pressure within the autoclave, substantial equality of pressure indicating that the steam has fully penetrated the load;
   (j) an axis of rotation which slopes forwardly and downwardly at an angle of 5-20°;
   (k) an axis of rotation slopes forwardly and downwardly at an angle of 10-15°;
   (l) the rotary autoclave supported by a support frame in a fixed attitude.

3. The rotary autoclave of claim 1, comprising door castellations and an autoclave rim provided with a locking ring,
   wherein the locking ring has lock blocks of inwardly facing U-configuration between which the door castellations can pass when the locking ring is in a release position and which as the locking ring is rotated to a closure position traps the door castellations against a protruding flange of the autoclave rim,
   the protruding flange running within an inner leg of the lock blocks, and
   the door castellations being received behind an outer leg of the lock blocks as the locking ring is rotated towards its closure position.

4. The rotary autoclave of claim 3, having one or more of the following features:
   (a) the locking ring comprises inner and outer annular plates between which the lock blocks are secured;
   (b) the inner annular plate carries roller bearings configured to run on a track on the autoclave rim for rotatably supporting the locking ring;
   (c) the inner leg of the lock blocks located within a groove of the autoclave rim;
   (d) the outer leg of the lock blocks and the door castellations have opposing wedge faces configured to cam the door towards the autoclave rim as the locking ring is rotated towards its closure position;

(e) the outer leg of the lock blocks are faced with a low friction material for contact with autoclave rim castellations;

(f) the inner leg of the lock blocks are faced with a low friction material for contact with the protruding flange;

(g) the facings of low friction material are removably attached to the outer leg;

(h) the low friction material is PTFE;

(i) the autoclave rim is formed with an outwardly protuberant frustoconical surface which opposes a corresponding surface of the door as the door is closed to align the door with the autoclave rim;

(j) the door is mounted to the rotary autoclave for linear travel when closer to the autoclave and for swinging travel when further from the autoclave.

5. The rotary autoclave of claim 1, in combination with at least one anaerobic digestion tank for digesting an organic-rich fraction of the autoclaved waste, a recovery system for recovering methane-containing gas from the at least one anaerobic digestion tank, at least one internal combustion engine for combusting the methane-containing gas and generating power, and a steam generator fed with combustion gas from the at least one internal combustion engine for generating and accumulating steam for supplying to the rotary autoclave.

6. The rotary autoclave of claim 5, having one or more of the following features:

(a) the steam generator comprises a steam accumulation tank;

(b) a recovery system for recovering jacket water from the at least one internal combustion engine, a first tank for water to be supplied to the rotary autoclave, a second tank for water to be supplied to the steam generator and heaters in the first and second tanks for heating the water therein to near boiling using the heat of said jacket water.

7. A method for treating solid waste which comprises:

introducing said solid waste into the interior of a rotary autoclave to form a load, said autoclave being downwardly inclined towards its discharge end and having a door at the discharge end for closing the rotary autoclave;

injecting steam for treating the load through said door via a plenum chamber in said door so that water and steam pass through at least one one-way device and then directly into the interior of the rotary autoclave, said at least one one-way device preventing the solid waste from entering the plenum chamber from the interior of the rotary autoclave;

said plenum chamber being defined between a region of the door and a plate secured to the door at a small spacing inwardly of said door;

at least one outlet being defined in the plate; and said at least one one-way device being fitted to said at least one outlet.

8. The method of claim 7, which comprises loading the solid waste into a top opening of the rotary autoclave whilst rotating the autoclave in a first direction in which screw flights within the autoclave convey the solid waste forwardly along a downwardly inclined body of the autoclave towards a base of the autoclave;

rotating the autoclave in a second direction opposite to the first direction so as to establish a circulation of the loaded waste material between the upper and lower ends of the rotary autoclave to facilitate vacuum and/or steam treatment thereof; and monitoring by means of load sensors the load distribution adjacent the upper and lower ends of the autoclave during the rotation in the second direction, increase of the load adjacent the upper end of the autoclave providing an indication of effective load circulation.

9. The method of claim 8, further comprising monitoring pressure at the upper and lower ends of the rotary autoclave, substantial equality of pressure indicating that the steam has fully penetrated the load and confirmation the entire load is at temperature.

10. The method of claim 7, wherein the steam is injected into the interior of the rotary autoclave through a plurality of one-way devices providing parallel paths from the plenum chamber into the interior of the autoclave.

11. The method of claim 10, wherein the cross-sectional area of the path or paths from the plenum chamber into the rotary autoclave defined by said at least one one-way device is equal to or greater than the area of an inlet for injected steam into the plenum chamber.

12. The method of claim 7, having one or more of the following features:

(a) injecting the steam into the rotary autoclave through at least one porous sintered metal disc leading from the plenum chamber into the autoclave;

(b) injecting the steam into the rotary autoclave through at least one mushroom or poppet valve or other one-way valve leading from the plenum chamber into the autoclave;

(c) injecting steam from a steam accumulator having a capacity for an accumulation of steam at a temperature and pressure effective to heat and fully penetrate the load;

(d) injecting recycled steam from a second autoclave which has substantially completed its treatment cycle;

(e) the rotary autoclave has generally helical internal flights, and which comprises rotating the generally helical internal flights during steam injection in a direction such that the flights lift the solid waste from the discharge end into the interior of the autoclave;

(f) monitoring load at upper and lower ends of the rotary autoclave while the generally helical internal flights are lifting the solid waste from the lower end, equalization of the load at the upper and lower ends compared to the loads at the upper and lower ends at the end of waste introduction indicating that lifting is taking place;

(g) introducing liquid water into the rotary autoclave as the load is introduced;

(h) the water that is introduced is near boiling;

(i) the water is introduced in an amount of 25-100 wt % based on the weight of the introduced load;

(j) the water is introduced in an amount of 25-50 wt % based on the weight of the introduced load;

(k) spraying water into the autoclave after steam injection for steam condensation; and/or (l) the amount of water sprayed into the autoclave is 25-50 wt % of the weight of the solid waste at the start of processing.

13. The method of claim 7, further comprising supplying an organic-rich fraction of processed solid waste from the rotary autoclave to an anaerobic digester, and recovering a methane-rich gas therefrom.

14. The method of claim 13, comprising:

steam autoclaving the solid waste to produce wet treated waste of solids content higher than that of the introduced solid waste e.g. 30-60 wt % water;

separating recyclables from an organic-rich aqueous fraction of the wet treated waste;

anaerobically digesting the organic-rich fraction;

recovering methane-containing gas from the anaerobic digestion;

internally combusting the methane-containing gas by means of an internal combustion engine to generate power and waste heat, and generating steam for autoclaving using the waste heat.

15. The method of claim 14, having one or more of the following features;
   (a) recovering heated jacket water from the internal combustion engine, and providing a stream derived from the heated jacket water to provide a warm feed for maintaining an elevated anaerobic digestion temperature;
   (b) the solid waste is food waste, slaughterhouse waste (optionally including slaughterhouse blood) or other protein-rich waste;
   (c) the solid waste is municipal solid waste or a sorted fraction thereof;
   (d) operating the anaerobic digester under mesophilic or thermophilic conditions.

* * * * *